(12) United States Patent
Plate et al.

(10) Patent No.: US 8,575,152 B2
(45) Date of Patent: Nov. 5, 2013

(54) NON-STEROIDAL COMPOUNDS USEFUL AS GLUCOCORTICOID RECEPTOR MODULATORS

(75) Inventors: Ralf Plate, Oss (NL); Christiaan Gerardus Johannes Maria Jans, Oss (NL)

(73) Assignee: Merck Sharp & Dohme B.V., BN Haarlem (NL)

( * ) Notice: Subject to any disclaimer, the term of this patent is extended or adjusted under 35 U.S.C. 154(b) by 1277 days.

(21) Appl. No.: 12/065,241

(22) PCT Filed: Aug. 25, 2006

(86) PCT No.: PCT/EP2006/065696
§ 371 (c)(1),
(2), (4) Date: Mar. 13, 2008

(87) PCT Pub. No.: WO2007/025938
PCT Pub. Date: Mar. 8, 2007

(65) Prior Publication Data
US 2008/0188459 A1 Aug. 7, 2008

(30) Foreign Application Priority Data
Aug. 29, 2005 (EP) ..................... 05107896

(51) Int. Cl.
*A61P 5/44* (2006.01)
*A61P 29/00* (2006.01)
*A61K 31/55* (2006.01)
*C07D 471/04* (2006.01)

(52) U.S. Cl.
USPC ..................... 514/214.01; 540/576

(58) Field of Classification Search
USPC ..................... 514/214.01; 540/576
See application file for complete search history.

(56) References Cited

U.S. PATENT DOCUMENTS

| | | | |
|---|---|---|---|
| 3,914,305 A | 10/1975 | Bruderlein et al. | |
| 4,016,161 A | 4/1977 | van der Burg | |
| 7,737,136 B2 * | 6/2010 | Hermkens et al. | 514/211.09 |

FOREIGN PATENT DOCUMENTS

| | | |
|---|---|---|
| EP | 1201655 A2 | 2/2005 |
| WO | WO2004/009017 A2 | 1/2004 |

* cited by examiner

*Primary Examiner* — Brenda Coleman
(74) *Attorney, Agent, or Firm* — Patricia A. Shatynski; Valerie J. Camara

(57) ABSTRACT

This invention relates to novel amino acid derivatives of formula (I) wherein the R groups have the following meanings: —$R_1$ is —H or —(1-4C)alkyl; —$R_2$ is —C(O)$R_{15}$ or —S(O)$_2R_{15}$; —$R_3$ is —H, —(1-4C)alkyl or —OR$_{16}$; —$R_4$ is —H, —(1-4C)alkyl or —OR$_{16}$; —$R_6$ is —H or —C($R_{16}$)NOR$_{16}$; —$R_7$ is —H, -halogen, -cyano; —(1-6C)alkyl, —(2-6C)alkenyl or —(2-6C)alkynyl, all optionally substituted with -amino, -hydroxyl or -halogen; —$R_8$ is —H, -cyano, -halogen, -nitro; —(1-6C)alkyl, —(2-6C)alkenyl, —(2-6C)alkynyl or —O(1-6C)alkyl, all optionally substituted with -amino, -hydroxyl or -halogen; -(hetero)aryl, optionally substituted with -cyano, -halogen, —(1-4C)alkyl, —(1-4C)alkoxy, —(1-4C)alkoxy(1-4C)alkyl or -(hetero)aryl; —C($R_{16}$)NOR$_{16}$; —C(O)N($R_{17}$)$_2$; —C(O)R18, —C(O)OR$_{19}$, —NHC(O)$R_{20}$, or —NHS(O)$_2R_{21}$; —$R_9$ is —H, -halogen, -cyano, or —(1-4C)alkyl, optionally substituted with -halogen; —$R_{10}$ is —H or —(1-4C)alkyl; —$R_{11}$ is —H; —$R_{12}$ is —H, -cyano or —(1-4C)alkyl; —$R_{13}$ is —H, —(1-4C)alkyl, -halogen or -formyl; —$R_{14}$ is —H, -halogen, -cyano, —(1-4C)alkyl or -(hetero)aryl; or a pharmaceutically acceptable salt thereof. The compounds of this invention are highly specific for the glucocorticoid receptor and may be used for treating inflammatory diseases.

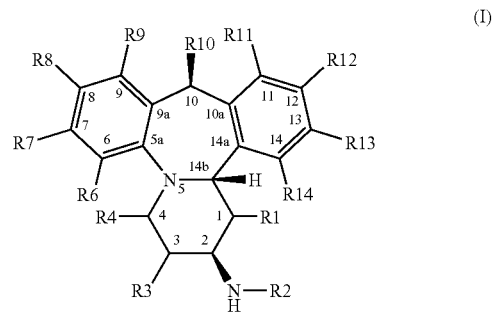

(I)

12 Claims, No Drawings

NON-STEROIDAL COMPOUNDS USEFUL AS GLUCOCORTICOID RECEPTOR MODULATORS

CROSS REFERENCE TO RELATED APPLICATION

This application claims priority based on International Patent Application No. PCT/EP2006/065696, filed on Aug. 25, 2006.

FIELD OF THE INVENTION

The present invention relates to glucocorticoid receptor modulating compounds as well as to the use of these compounds in therapy.

BACKGROUND OF THE INVENTION

Intracellular receptors are a class of structurally related proteins involved in the regulation of gene proteins. Steroid receptors are a subset of these receptors, including the glucocorticoid receptor (GR), progesterone receptor (PR), androgen receptor (AR), estrogen receptor (ER), and mineralocorticoid receptor (MR). Regulation of a gene by such receptors or factors requires the intracellular receptor and a corresponding ligand which has the ability to selectively bind to the receptor in a way that affects gene transcription.

The current steroidal glucocorticoid receptor modulators (glucocorticoids) like prednisolone a.o. are very effective anti-inflammatory agents that are currently used to treat diseases like Rheumatoid Arthritis (RA), Inflammatory Bowel Disease (IBD), Lupus, allergies, asthma, psoriasis and to prevent transplant rejection (J. D. Baxter, Advances in Internal Medicine 45; 317-349; 2000). Anti-inflammatory effects of these compounds are thought to be mediated through an inhibition of the expression of pro-inflammatory mediators like adhesion molecules, cytokines, chemokines and enzymes by a mechanism that involves the interaction of the ligand-bound GR with transcription factors. This mechanism is referred to as transrepression (M. Karin, Cell 93; 487-490; 1998).

The use of current steroidal glucocorticoids is accompanied by metabolic and other side effects (e.g. diabetes, hypertension, osteoporosis, muscle wasting, a.o.). Part of these side effects are thought to be mediated through the direct interaction of the ligand bound GR to glucocorticoid responsive elements (GRE's) on the DNA of target genes and the subsequent induction of gene expression (J. D. Baxter, Advances in Internal Medicine 45; 317-349; 2000; M. Karin, Cell 93;487-490; 1998). Another part of these side effects might be due to cross-reactivity with other steroidal receptors, like the mineralcorticoid (MR) or the progesterone receptor (PR).

Non-steroidal glucocorticoids have no molecular structural similarity with steroids and therefore one might also expect differences in physicochemical properties, pharmacokinetics (PK) parameters, tissue distribution (e.g. CNS versus peripheral) and more importantly non-steroidal glucocorticoids may show no/less cross-reactivity to other steroid receptors or may show no/less metabolic or other side effects.

DETAILED DESCRIPTION OF THE INVENTION

The present invention provides non-steroidal compounds that modulate glucocorticoid receptor activity. More particularly, the present invention provides high affinity non-steroidal compounds for GR binding which show anti-inflammatory effects in vitro and in vivo. According to the present invention compounds are provided having a general formula I, or a prodrug thereof, or a pharmaceutically acceptable salt thereof.

The present invention provides non-steroidal compounds that modulate glucocorticoid receptor activity. More particularly, the present invention provides high affinity non-steroidal compounds which are agonist, partial agonists or antagonists of the glucocorticoid receptor. According to the present invention compounds are provided having a general Formula I,

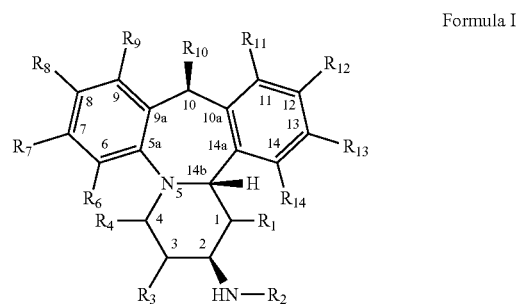

Formula I or a pharmaceutically acceptable salt thereof.

In this formula the R groups have the following meanings:
- $R_1$ is —H or —(1-4C)alkyl;
- $R_2$ is —C(O)$R_{15}$ or —S(O)$_2R_{15}$;
- $R_3$ is —H, —(1-4C) alkyl or —O$R_{16}$;
- $R_4$ is —H, —(1-4C)alkyl or —O$R_{16}$;
- $R_6$ is —H or —C($R_{16}$)NO$R_{16}$;
- $R_7$ is —H, -halogen, -cyano;
- —(1-6C) alkyl, —(2-6C)alkenyl or —(2-6C)alkynyl, all optionally substituted with -amino, -hydroxyl or -halogen;
- $R_8$ is —H, -cyano, -halogen, -nitro;
- —(1-6C)alkyl, —(2-6C)alkenyl, —(2-6C)alkynyl or —O(1-6C)alkyl, all optionally substituted with -amino, -hydroxyl or -halogen;
- -(hetero)aryl, optionally substituted with -cyano, -halogen, —(1-4C)alkyl, —(1-4C)alkoxy, —(1-4C)alkoxy(1-4C)alkyl or -(hetero)aryl;
- —C($R_{16}$)NO$R_{16}$, —C(O)N($R_{17}$)$_2$, —C(O)$R_{18}$, —C(O)O$R_{19}$, —NHC(O)$R_{20}$ or —NHS(O)$_2R_{21}$;
- $R_9$ is —H, -halogen, -cyano, or —(1-4C)alkyl, optionally substituted with -halogen;
- $R_{10}$ is —H or —(1-4C)alkyl;
- $R_{11}$ is —H;
- $R_{12}$ is —H, -cyano or —(1-4C)alkyl;
- $R_{13}$ is —H, —(1-4C)alkyl, -halogen or -formyl;
- $R_{14}$ is —H, -halogen, -cyano, —(1-4C)alkyl or -(hetero)aryl;
- $R_{15}$ is —H;
- —(1-6C)alkyl, —(2-6C)alkenyl, —(2-6C)alkynyl, -O(2-6C)alkyl, —O(2-6C)alkenyl or —O(2-6C)alkynyl, all optionally substituted with one or more —OH, -halogen, -cyano or -(hetero)aryl;
- -(hetero)aryl, optionally substituted with —(1-4C)alkyl, -halogen or —NH$_2$;
- —NH$_2$, —(di)(1-4C)alkylamino, —(1-4C)alkylthio(1-4C)alkyl, —(1-4C)alkoxy(1-4C)alkyl or —N$R_{16}$O$R_{16}$;
- $R_{16}$ is —H, —(1-6C)alkyl, —(2-6C)alkenyl or —(2-6C)alkynyl;
- $R_{17}$ is —H;

—(1-6C)alkyl, optionally substituted with halogen, —(1-4C)alkoxy or -(hetero)aryl, optionally substituted with -halogen, —(1-4C)alkyl or —(1-4C)alkoxy;

—(3-6C)cycloalkyl or -(hetero)aryl, optionally substituted with -halogen, —(1-4C)alkyl or —(1-4C)alkoxy;

—$R_{18}$ is —H, —$NH_2$ or —(1-4C)alkyl, optionally substituted with —OH, -halogen, -cyano or —S(1-4C)alkyl;

—$R_{19}$ is —H or —(1-6C)alkyl, optionally substituted with —OH or -halogen;

—$R_{20}$ is —H;

—(1-6C)alkyl or —(2-6C)alkenyl, both optionally substituted by -halogen, —O(1-6C)alkyl, -(hetero)aryl, optionally substituted with —(1-4C)alkyl or -halogen;

—(3-6C)cycloalkyl, —(1-6C)alkoxy, —(1-6C)alkenyloxy;

-(hetero)aryl, optionally substituted with —(1-4C)alkyl);

—$NH_2$, —NH(1-6C)alkyl or —NH((hetero)aryl) and

—$R_{21}$ is —H or —(1-6C)alkyl.

Thus, it has now been found, that the foregoing class of compounds according to Formula I or pharmaceutically acceptable salts thereof, have glucocorticoid receptor modulatory activity.

The term —(1-6C)alkyl as used in the definition of the invention means a branched or unbranched alkyl group having 1-6 carbon atoms, for example methyl, ethyl, propyl, isopropyl, butyl, sec-butyl and tert-butyl, pentyl and hexyl. Preferred are —(1-4C)alkyl. The term —(1-4C)alkyl as used in the definition of the invention means a branched or unbranched alkyl group having 1-4 carbon atoms, for example methyl, ethyl, propyl, isopropyl, butyl, sec-butyl and tert-butyl. Preferred are methyl and ethyl. Most preferred is methyl.

The term —(3-6C)cycloalkyl means a cyclic alkyl group having 3-6 carbon atoms.

The term halogen means fluorine, chlorine, bromine or iodine.

The term —(2-6C)alkenyl means a branched or unbranched alkenyl group having 2-6 carbon atoms, such as ethenyl, 2-butenyl, pentenyl and hexenyl. Preferred are —(2-4C)alkenyl.

The term —(2-4C)alkenyl means a branched or unbranched alkenyl group having 2-4 carbon atoms, such as ethenyl and 2-butenyl.

The term —(2-6C)alkynyl means a branched or unbranched alkynyl group having 2-6 carbon atoms, such as ethynyl, propynyl, butylyl, pentynyl and hexynyl. Preferred are —(2-4C)alkynyl.

The term —(2-4C)alkynyl means a branched or unbranched alkynyl group having 2-4 carbon atoms, such as ethynyl and propynyl.

The term —O(1-6C)alkyl means —(1-6C)alkyloxy wherein —(1-6C)alkyl has the previously defined meaning.

The term —O(2-6C)alkenyl means —(2-6C)alkenyloxy wherein —(2-6C)alkenyl has the previously defined meaning.

The term —O(2-6C)alkynyl means —(2-6C)alkynyloxy wherein —(2-6C)alkynyl has the previously defined meaning.

The term —(1-4C)alkyloxy means an alkyloxy group having 1-4 carbon atoms, the alkyl moiety having the same meaning as previously defined. —(1-2C)Alkyloxy groups are preferred. Most preferred is methoxy.

The term —(1-4C)alkoxy(1-4C)alkyl means a —(1-4C)alkoxy attached to a —(1-4C)alkyl group, both groups having the previously defined meanings.

The term —(di)(1-4C)alkylamino means a amino moiety, with at least one, optionally two hydrogens replaced by a —(1-4C) alkyl group as previously defined.

The term —S(1-4C)alkyl means a —(1-4C)alkylthio group, the —(1-4C)alkyl group having the previously defined meaning.

The term —NH(1-6C)alkyl means a —(1-6C)alkylamine group, the —(1-6C)alkyl group having the previously defined meaning.

The term —NH(hetero)aryl means a -(hetero)arylamine group, the -(hetero)aryl group having the previously identified meaning.

The term —(1-4C)alkylthio(1-4C)alkyl means an —(1-4C)alkylthio group attached to a —(1-4C)alkyl group, both having the previously defined meanings.

The term aryl means 6 membered aromatic ring system.

The term -(hetero)aryl means a 5 or 6 membered aromatic ring system containing at least one heteroatom selected from the group of N, O and S, such as, but not limited to, pyridinyl, pyrimidinyl, pyrazinyl, tetrazolyl, thiadiazolyl, isoxazolyl, oxadiazolyl, dihydrooxazolyl or furanyl.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, meleic acid, malonic acid, fumario acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The invention thus relates to the compounds of formula I as defined here above.

Another aspect of the invention concern the compounds according to Formula I wherein —$R_3$, —$R_5$, —$R_7$, —$R_9$, —$R_{12}$, —$R_{13}$, —$R_{14}$ are —H and —$R_4$ and —$R_{16}$ are —H or —(1-4C)alkyl and the other groups have the indicated meaning.

Another aspect of the invention is directed compounds according to Formula I wherein —$R_1$ is —H;

—$R_8$ is —H, -cyano or -halogen;

-(hetero)aryl, optionally substituted with —(1-4C)alkyl;

—$C(R_{16})NOR_{16}$, —$C(O)N(R_{17})_2$, —$C(O)R_{18}$ or —$C(O)OR_{19}$;

—$R_{10}$ is —(1-4C)alkyl;

—$R_{15}$ is —(1-6C)alkyl, optionally substituted with one or more -halogen or -(hetero)aryl;

-(hetero)aryl, optionally substituted with —(1-4C)alkyl or —$NH_2$; or —(di)(1 -4C)alkylamino;

—$R_{17}$ is -(hetero)aryl, optionally substituted with —(1-4C)alkoxy;

—$R_{18}$ is —(1-4C)alkyl and

—$R_{19}$ is —(1-6C)alkyl.

In yet another aspect the invention concerns compounds according to Formula I wherein —$R_8$ is -cyano, -(hetero)aryl, optionally substituted with —(1-4)alkyl;

—$CO(N)R_{17}$, —$C(O)R_{18}$ or —$C(O)OR_{19}$.

In a further aspect the invention relates to compounds according to Formula I wherein
—(hetero)aryl in —$R_8$ is a 6-membered heteroaromatic ring.

In still a further aspect the invention relates to compounds according to Formula I wherein the heteroaromatic ring in —(hetero)aryl in —$R_8$ contains 1 or more N atoms.

In yet another aspect the invention is directed to compounds according to Formula I wherein —$R_2$ is —$C(O)R_{15}$.

In a further aspect the invention relates to compounds according to Formula I wherein —$R_{15}$ is a -5-membered (hetero)aryl.

In another aspect the invention relates to compounds according to Formula I wherein —$R_{15}$ is a —(1-4C)alkyl, optionally substituted with one or more halogen.

The invention also resides in compounds according to Formula I which are highly specific for the glucocorticoid receptor. Specificity can be determined by testing the compound as described further on for the glucocorticoid receptor, with other well-known receptors such as progesterone receptor, androgen receptor, mineralocorticoid receptor or estrogen receptor.

Furthermore, the present invention covers all possible combinations of particular and preferred groups described hereinabove.

The compounds of the present invention possess at least three chiral carbon atoms and may therefore be obtained as pure enantiomers, or as a mixture of enantiomers, or as a mixture of diastereomers. Methods for obtaining the pure enantiomers are known in the art, e.g crystallization of salts which are obtained from optically active acids and the racemic mixture, or chromatography using chiral columns. For separation of diastereomers, straight phase or reversed phase columns may be used.

The compounds of the present invention can be synthesized in a sequence of reaction steps as shown in steps A through I.

Step A
Treatment of anthraquinone (1) with sodium azide in concentrated sulfuric acid gives access to the desired 5H-dibenzo[b,e]azepine-6,11-dione (2) in quantitative yield (Scheme 1)

Step B
Compounds of general structure 2 can then be methylated to afford compounds of general structure 3.

Step C
Compounds of general structure 3 can then be reduced to afford compounds of general structure 4. The above mentioned reaction is typically conducted using lithium aluminium hydride as reagent.

Step D
Compounds of general structure 4 can then be selectively oxidized to afford the morphantridine derivative 5.

The above mentioned reaction is typically conducted at ambient temperature in the presence of manganese dioxide.

Steps E,F
Compounds of general structure 5 can then be reacted in a Diels-Alder fashion to form ring D and afford tetracyclic compounds of general structure 6. These compounds can then be reduced in-situ to afford the tetracyclic alcohols of general structure 7, which are obtained mainly in the trans conformation.

The first above mentioned reaction is typically conducted at reduced temperature in the presence of Danishefsky's diene and ytterbium trifluoromethanesulfonate, with the use of an organic solvent. These crude products are then reduced at ambient temperature in the presence of sodium borohydride, with the use of an organic solvent.

Step G
Compounds of general structure 7 can then be reacted under Mitsunobu conditions to afford azide compounds of general structure 8.

The above mentioned reaction is typically conducted at ambient temperature in the presence of triphenylphosphine, diisopropylazodicarboxylate and diphenylphosphoryl azide, with the use of an organic solvent.

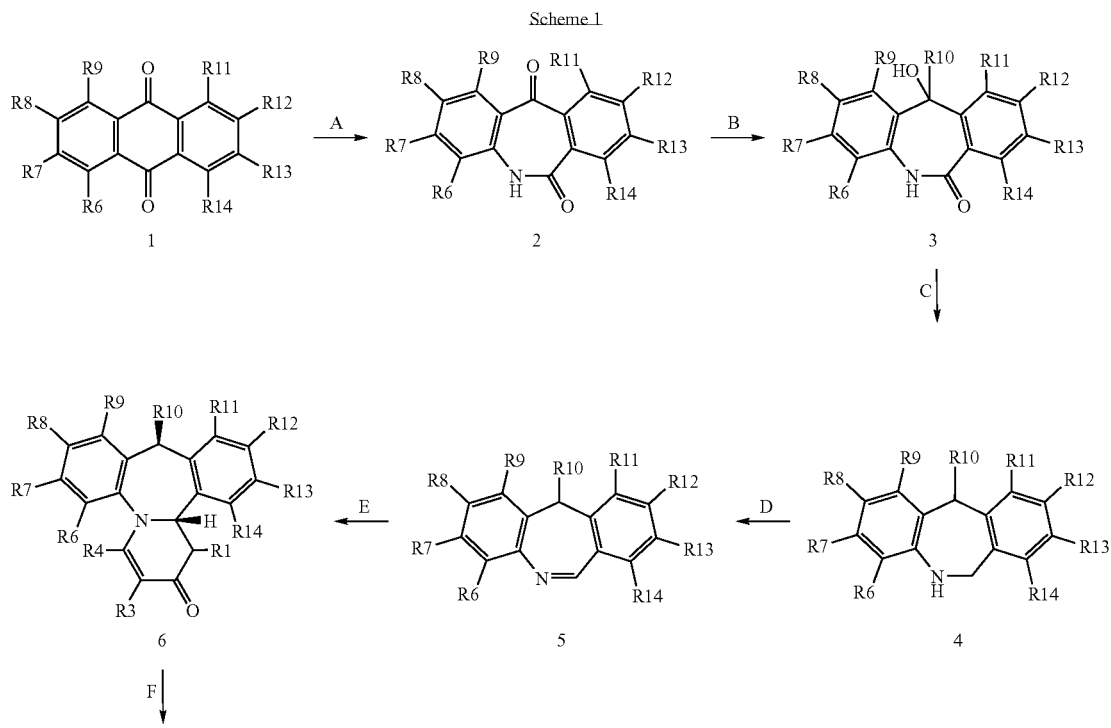

Scheme 1

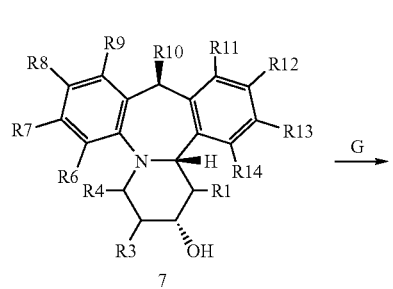 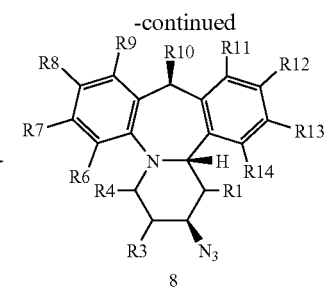 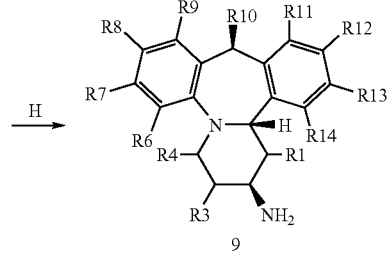

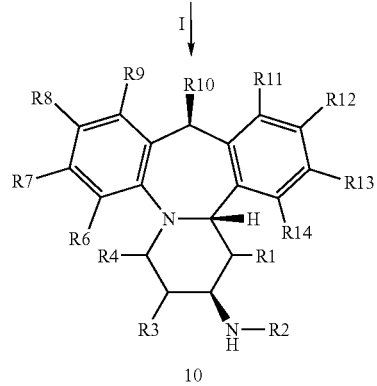

Step H

Compounds of general structure 8 can then be reduced to afford the free amine compounds of general structure 9. The above mentioned reaction is typically conducted at ambient temperature in the presence of triphenylphosphine and water, with the use of an organic solvent.

Step I

These products 9 are then converted into the desired amides, carbamates and urea's and sulphonamides 10 by general procedures.

Compounds 7, 9 and 10 are the key intermediate compounds in the formation of all other compounds disclosed within. These compounds, either already being halogenated or can be halogenated, etc. and then further modified by the methods described within to afford the desired entities with the desired rel-(2R,10R,14bR)-stereochemistry.

The compounds of the present invention possess at least three chiral carbon atoms and may therefore be obtained as pure enantiomers, or as a mixture of enantiomers, or as a mixture of diastereomers. Methods for obtaining the pure enantiomers are known in the art, e.g crystallization of salts which are obtained from optically active acids and the racemic mixture, enzymatic resolution proceedings or chromatography using chiral columns. For separation of diastereomers, straight phase or reversed phase columns may be used.

It has been found that eutomers have (2S,10S,14bS)-stereochemistry.

The compounds of the present invention modulate glucocorticoid receptor activity. The compounds thus can be used in the treatment of immunological and inflammatory diseases. In particular the compounds can be used to treat rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease, and other immune and inflammatory diseases including Crohn disease, ulcerative colitis, systemic lupus erythematosus, autoimmune chronic active hepatitis, osteoarthritis, tendonitis, and bursitis. In addition, the compounds can be used to help prevent rejection of organs after organ transplantation.

More in particular the compounds can be used to treat rheumatoid arthritis, psoriasis, asthma and chronic obstructive pulmonary disease, Crohn disease or ulcerative colitis and the compounds can be used to help prevent rejection of organs after organ transplantation.

Methods to determine receptor binding as well as in vitro and in vivo assays to determine biological activity of the compounds are well known in the art. In general, the expressed receptor is treated with the compound to be tested and binding, stimulation or inhibition of a functional response is measured.

To measure binding, isolated cytosol containing the expressed GR may be used. Radioactive or fluorescence labelled compounds may also be used. As reference compound, native hormone or other compounds binding to the receptor can be used. As an alternative, also competition binding assays can be performed. These binding assays can be either developed in house or might be purchased as commercially available binding assays (kits). Experimental methods to determine binding affinities are well known in the art.

For selecting GR modulators, compounds should bind with an affinity of $<10^{-5}$ M to the receptor. More preferably, binding affinity is $<10^{-7}$ M and most preferably, binding affinity is $<10^{-8}$ M.

To measure a functional response, isolated DNA encoding the glucocorticoid receptor gene, preferably the human receptor, is expressed in suitable host cells, for instance in human osteoblastic U2OS cells.

Methods to construct recombinant glucocorticoid receptor-expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR and construction of suitable expression systems are all, by now, well known in the art. Portions or the entire DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts, such as bacteria, and eukaryotic hosts, such as yeast, plant cells, insect cells, mammalian cells, avian cells and the like.

In vitro, inflammation can be mimicked in a human cell line, stably transfected with human GR DNA that is stimulated to secrete cytokines, chemokines and other inflammatory mediators. Anti-inflammatory effects of compounds can be quantified by measuring inhibition of the inflammatory response in that cell line. By testing full dose response curves, $EC_{50}$ values can be calculated for both compounds and a reference compound like prednisolone. $EC_{50}$ values might be compared to the $EC_{50}$ values obtained for prednisolone within the same cellular assay. Preferably compounds have $EC_{50}$ values that are in the range of the $EC_{50}$ obtained for prednisolone. More preferably, $EC_{50}$ values are less than that obtained for prednisolone.

The skilled artisan will recognize that desirable $EC_{50}$ values are dependent on the compound tested. For example, a compound with an $EC_{50}$, which is less than $10^{-5}$ M is, generally, considered a candidate for drug selection. Preferably this value is lower than $10^{-7}$ M. However, a compound which has a higher $EC_{50}$, but is selective for the particular receptor, may be even a better candidate.

In vivo, the anti-inflammatory effect of compounds can be tested in mice that are treated with lipopolysaccharide (LPS). Compounds can be administered systemically at or before the time of LPS treatment. Anti-inflammatory effects can be quantified as an inhibition of LPS-induced TNFα in the serum of mice or any other inflammatory cytokine or chemokine (S. R. Hyde & R. E. McCallum, Infection and Immunity, 60; 976-982(1992)). The potency to inhibit arthritis could be tested in the mouse collagen type II-induced arthritis model (CIA) as the ability to inhibit paw swelling (D. E. Trentham et al. J. Exp Med 146; 857-868 (1977)), or another arthritis model.

The invention thus also resides in a pharmaceutical composition comprising a compound or a salt thereof having the general formula I. Thus, the compounds according to formula I can be used in therapy.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (e.g. treatment of asthma, R.A, I.B.D) and may vary with the particular compound, the route of administration, and the age and condition of the individual subject to whom the medicament is to be administered. Generally, a therapeutically effective daily dose is from about 0.001 mg to about 15 mg/kg of body weight per day per compound of the invention; preferably, from about 0.1 mg to about 10 mg/kg of body weight per day; and most preferably, from about 0.1 mg/kg to about 1.5 mg/kg of body weight per day. Some degree of routine dose optimization may be required to determine an optimal dosing level and pattern.

Administration of the compounds of the invention, in pure form or in an appropriate pharmaceutical composition, can be carried out using any of the accepted modes of administration of pharmaceutical compositions. Thus, administration can be, for example, orally, bucally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosage.

A further aspect of the invention resides in the use of the compounds according to Formula I or a pharmaceutically acceptable salt or solvate thereof for the preparation of a medicament for immunotherapy.

EXAMPLES

The numbering in the examples refers to Scheme 1, where $R_1$, $R_3$, $R_4$, $R_6$-$R_9$=H, $R_{10}$=Me, $R_{11}$-$R_{14}$=H, unless stated otherwise.

A mixture of concentrated sulfuric acid (25.2 mL) and DCM (dichloromethane) (8.4 mL) was cooled to 0° C., anthraquinone (1) (5 g, 24 mmol) was added, then sodium azide (1.84 g, 28.3 mmol) was added in small portions over a 1 h period at 0-5° C. The reaction mixture stirred overnight at room temperature and then poured into ice water (300 mL). The product was filtered off, washed with water till acid-free and dried to give 5H-dibenzo[b,e]azepine-6,11-dione (2) as a white solid (5.3 g, 100%). Data: (m/z)=224 (M+H)$^+$.

To a suspension of 5H-dibenzo[b,e]azepine-6,11-dione (2) (50 g, 0.22 mol) in toluene (800 mL) methyl magnesium iodide (3 M in Et$_2$O, 200 mL, 0.6 mol) was added. The reaction mixture was heated under reflux for 6 h, then poured into aqueous ammonium chloride and stirred for 10 minutes. The product was filtered off and dried to give 11-hydroxy-11-methyl-5,11-dihydro-dibenzo[b,e]azepin-6-one (3) as a white solid (51.6 g, 96%). Data: (m/z)=240 (M+H)$^+$.

11-Hydroxy-11-methyl-5,11-dihydro-dibenzo[b,e]azepin-6-one (3) (51.6 g 0.22 mol) was added to a suspension of LiAlH$_4$ (33 g, 0.88 mol) in dioxane (850 mL). The reaction mixture was heated to 105° C. After 2.5 h under reflux the reaction mixture was cooled, the excess LiAlH$_4$ was destroyed with aqueous Na$_2$SO$_4$ (55 mL). ethyl acetate (1.81) and Na$_2$SO4 (440 g) were added, the reaction mixture was stirred for 30 min. The solids were filtered off and the filtrate was concentrated under reduced pressure. The crude product was purified by column chromatography on silica (Heptane:Ethyl acetate=6:4) to give 6,11-dihydro-11-methyl-5H-dibenzo[b,e]azepine (4) (28 g, 61%) Data: (m/z)=210 (M+H)$^+$.

A solution of 6,11-dihydro-11-methyl-5H-dibenzo[b,e]azepine (4) (8 g, 38.3 mmol) in aceton (1500 mL) was cooled to 0° C. and NBS (N-bromosuccinamide; 6.81 g, 38.3 mmol) was added. The reaction mixture was stirred for 20 min at 0° C., quenched by addition of aqueous NaHCO$_3$ (300 mL) and concentrated under reduced pressure. The product was extracted into ethyl acetate which was washed with brine, dried (Na$_2$SO$_4$) and concentrated under reduced pressure. The crude product was purified by column chromatography on silica (Heptane:Ethyl acetate=8:2) to give 2-bromo-6,11-dihydro-11-methyl-5H-dibenzo[b,e]azepine (4, $R_8$=Br; 32 g, 97%) Data: (m/z)=288/290 (M+H)$^+$.

To a solution of 2-bromo-6,11-dihydro-11-methyl-5H-dibenzo[b,e]azepine (4, $R_8$=Br; 32 g, 0.11 mol) in DCM, $MnO_2$ (manganese oxide)(96.6 g, 1.11 mol) was added and the reaction mixture was allowed to stir overnight. The reaction mixture was filtered over decalite and concentrated under reduced pressure. The crude product was purified by column chromatography on silica (Heptane:Ethyl acetate=8:2) to give 2-bromo-11-methyl-11H-dibenzo[b,e]azepine (5, $R_8$=Br; 29.4 g, 92%). Data: (m/z)=286/288 (M+H)$^+$.

To a stirred solution of 2-bromo-11-methyl-11H-dibenzo[b,e]azepine (5$R_8$=Br; 666 mg, 2.33 mmol) ytterbium (III) triflate (146 mg, 0.23 mmol) was added. After stirring for 10 min. at room temperature Danishefsky's diene (0.89 mL, 4.66 mmol) was added. The reaction mixture was allowed to stand overnight at room temperature. The reaction mixture was quenched with aqueous $NaHCO_3$, extracted into ethyl acetate, washed with brine, dried ($Na_2SO_4$) and concentrated under reduced pressure. The crude product was purified by column chromatography on silica to give 8-bromo-10,14b-dihydro-10-methyl-dibenzo[c,f]pyrido[1,2-a]azepin-2(1H)-one (6, $R_8$=Br; 338 mg, 41%). Data: (m/z)=354/356 (M+H)$^+$.

A suspension of 8-bromo-10,14b-dihydro-10-methyl-dibenzo[c,f]pyrido[1,2-a]azepin-2(1H)-one (6, $R_8$=Br; 13.07 g, 37 mmol) in ethanol (700 mL) was cooled to 0° C. and $NaBH_4$ (14 g, 370 mmol) was added. The reaction mixture was stirred overnight at room temperature. The reaction mixture was cooled, the excess $NaBH_4$ was destroyed with aceton (300 mL), stirred for 30 min. and concentrated under reduced pressure. The product was extracted with ethyl acetate and aqueous $NH_4Cl$, washed with brine, dried ($Na_2SO_4$) and concentrated under reduced pressure. The crude product was purified by column chromatography on silica (Heptane:Ethyl acetate=7:3) to give rel-[(2R,10R,14bR)-8-bromo-1,2,3,4,10,14b-hexahydro-10-methyl-dibenzo[c,f]pyrido[1,2-a]azepin-2(1H)-ol (7, $R_8$=Br; 7.8 g, 60%). Data: (m/z)=358/360 (M+H)$^+$.

A stirred solution of rel-[(2R,10R,14bR)-8-bromo-1,2,3,4,10,14b-hexahydro-10-methyl-dibenzo[c,f]pyrido[1,2-a]azepin-2(1H)-ol (7, $R_8$=Br; 5.0 g, 14 mmol) and triphenylphosphine (4.76 g, 18.1 mmol) in dry THF (150 mL) was cooled to 0° C. and diisopropylazodicarboxylate (3.60 mL, 18.1 mmol) was added. Diphenylphosphorylazide (3.90 mL, 18.1 mmol) was added, then the cooling was removed. The reaction was allowed to warm to ambient temperature and stirred overnight. The reaction mixture was concentrated under reduced pressure and the crude product was purified by column chromatography on silica (Heptane:Ethyl acetate=95:5) to afford rel-[(2R,10R,14bR)-2-azido-8-bromo-1,2,3,4,10,14b-hexahydro-10-methyl-dibenzo[c,f]pyrido[1,2-a]azepine (8, $R_8$=Br; 4.7 g, 89%). Data: (m/z)=383/385 (M+H)$^+$.

To a stirred solution of rel-[(2R,10R,14bR)-2-azido-8-bromo-1,2,3,4,10,14b-hexahydro-10-methyl-dibenzo[c,f]pyrido[1,2-a]azepine (8, $R_8$=Br; 4.7 g, 12.3 mmol) in THF (150 mL) and $H_2O$ (4.5 mL) triphenylphosphine (3.86 g, 14.7 mmol) was added. The reaction mixture was stirred overnight at 50° C. then concentrated under reduced pressure to afford rel-[(2R,10R,14bR)-8-bromo-1,2,3,4,10,14b-hexahydro-10-methyl-dibenzo[c,f]pyrido[1,2-a]azepin-3-amine (9, $R_8$=Br). Data: (m/z)=357/359 (M+H)$^+$.

Example 1

Rel-N-[(2R,10R,14bR)-8-bromo-1,2,3,4,10,14b-hexahydro-10-methyldibenzo[c,f]pyrido[1,2-a]azepin-2-yl]-2,2,2-trifluoroacetamide (10, $R_8$=Br, $R_2$=COCF$_3$)

Crude 9 ($R_3$=Br) was taken up in MeOH (150 mL), triethylamine (3.4 mL, 24.6 mmol) and ethyltrifluoroacetate (7.33 mL, 61.5 mmol) were added and the reaction mixture was heated to 50° C. and held for 3 hours. The reaction mixture was concentrated under reduced pressure then purified by column chromatography on silica (Heptane:Ethyl acetate=8:2) to afford rel-N-[(2R,10R,14bR)-8-bromo-1,2,3,4,10,14b-hexahydro-10-methyldibenzo[c,f]pyrido[1,2-a]azepin-2-yl]-2,2,2-trifluoroacetamide (10, $R_8$=Br, $R_2$=COCF$_3$; 4.7 g, 84%). Data: (m/z)=453/455 (M+H)$^+$.

Example 2

Rel-N-[(2R,10R,14bR)-8-cyano-1,2,3,4,10,14b-hexahydro-10-methyldibenzo[c,f]pyrido[1,2-a]azepin-2-yl]-2,2,2-trifluoroacetamide (10, $R_8$=CN, $R_2$=COCF$_3$)

A stirred solution of 10 ($R_8$=Br, $R_2$=COCF$_3$; 800 mg, 1.77 mmol) in NMP (N-methylpyrrolidone) (15 mL) was degassed by bubbling nitrogen through for 0.5 hours. CuCN (395 mg, 4.43 mmol) was added and the reaction mixture was stirred for 7 hours at 200° C. The reaction mixture was quenched with a 25% $NH_4OH$ solution in $H_2O$ and the product was extracted into ethyl acetate. The organics were washed with a to 25% solution of $NH_4OH$ in $H_2O$, brine, dried ($Na_2SO_4$) and concentrated under reduced pressure. The crude product was purified by column chromatography on silica (Heptane:Ethyl acetate=8:2) to rel-N-[(2R,10R,14bR)-8-cyano-1,2,3,4,10,14b-hexahydro-10-methyldibenzo[c,f]pyrido[1,2-a]azepin-2-yl]-2,2,2-trifluoroacetamide (10, $R_8$=CN, $R_2$=COCF$_3$; 630 mg, 89%). Data: (m/z)=400 (M+H)$^+$.

Example 3

Rel-2,2-dichloro-N-[(2R,10R,14bR)-8-cyano-1,2,3,4,10,14b-hexahydro-10-methyldibenzo[c,f]pyrido[1,2-a]azepin-2-yl]acetamide (10, $R_8$=CN, $R_2$=CHCl$_2$)

To a stirred solution of 10 ($R_8$=CN; $R_2$=COCF$_3$; 78 mg, 0.195 mmol) in EtOH (5 mL) was added a 2N NaOH solution in $H_2O$ (1 mL). The reaction mixture was stirred at room temperature for 2 hours. The reaction was quenched with $H_2O$ and extracted with ethyl acetate. The organics were washed with brine, dried ($Na_2SO_4$) and concentrated under reduced pressure to afford crude rel-N-[(2R,10R,14bR)-8-cyano-1,2,3,4,10,14b-hexahydro-10-methyl-dibenzo[c,f]pyrido[1,2-a]azepin-3-amine (9, $R_8$=CN; 60 mg, 100%).

A stirred solution of 9 ($R_8$=CN; 108 mg, 0.356 mmol) and triethylamine (52 mL, 0.374 mmol) in DCM (4 mL) was cooled to 0° C. Dichloroacetyl chloride (36 mL, 0.374 mmol) was added and the reaction was stirred at room temperature for 2 hours. The reaction was quenched with a saturated $NaHCO_3$ solution in $H_2O$ and the product was extracted into DCM. The organics were dried and concentrated under reduced pressure. The crude product was purified by column chromatography on silica, followed by preparative HPLC. Freeze-drying from EtOH/$H_2O$ afforded rel-2,2-dichloro-N-[(2R,10R,14bR)-8-cyano-1,2,3,4,10,14b-hexahydro-10-methyldibenzo[c,f]pyrido[1,2-a]azepin-2-yl]acetamide (10, $R_8$=CN, $R_2$=COCHCl$_2$; 64 mg, 46%). Data: (m/z)=415 (M+H)$^+$.

Example 4

Rel-2,2,2-trifluoro-N-[(2R,10R,14bR)-1,2,3,4,10,14b-hexahydro-10-methyldibenzo[c,f]pyrido[1,2-a]azepin-2-yl]acetamide (10: $R_2$=CF$_3$)

This compound was prepared, in an analogous manner as described in Example 1, from 5 to afford rel-2,2,2-trifluoro- N-[(2R,10R,14bR)-1,2,3,4,10,14b-hexahydro-10-methyldibenzo[c,f]pyrido[1,2-a]azepin-2-yl]acetamide (10: $R_2$=$CF_3$). Data: (m/z)=375 (M+H)$^+$.

Example 5

Rel-N-[(2R,10R,14bR)-8-cyano-1,2,3,4,10,14b-hexahydro-10-methyldibenzo[c,f]pyrido[1,2-a]azepin-2-yl]-4-methyl-1,2,3-thiadiazole-5-carboxamide (10: $R_8$=CN, $R_2$=$COC_3H_3N_2S$)

This compound was prepared, in an analogous manner as described in Example 3, from 9 ($R_8$=CN) to afford rel-N-[(2R,10R,14bR)-8-cyano-1,2,3,4,10,14b-hexahydro-10-methyldibenzo[c,f]pyrido[1,2-a]azepin-2-yl]-4-methyl-1,2,3-thiadiazole-5-carboxamide (10: $R_8$=CN, $R_2$=$COC_3H_3N_2S$; 434 mg, 61%). Data: (m/z)=430 (M+H)$^+$.

Example 6

Rel-N-[(2R,10R,14bR)-8-cyano-1,2,3,4,10,14b-hexahydro-10-methyldibenzo[c,f]pyrido[1,2-a]azepin-2-yl]-2,2-difluoroacetamide (10: $R_8$=CN, $R_2$=$COCHF_2$)

To a solution of difluoroacetic acid (8.5 μl, 0.135 mmol) in DCM (1 mL), TBTU (O-(Benzotriazol-1-yl)-N,N,N',N'-tetramethyluronium tetrafluoroborate) (51 mg, 0.159 mmol) and DIPEA (N,N-Diisopropylethylamine) (26 μl, 0.149 mmol) were added and the reaction mixture was stirred at room temperature. After 10 minutes a solution of 9 ($R_8$=CN; 25 mg, 0.082 mmol) in DCM (1 mL) was added. The reaction mixture was stirred overnight at room temperature. The reaction was quenched with a saturated $NaHCO_3$ solution in $H_2O$ and extracted with DCM. The organic layer was dried ($Na_2SO_4$) and the organics were concentrated under reduced pressure. The crude product was purified with column chromatography on silica to afford rel-N-[(2R,10R,14bR)-8-cyano-1,2,3,4,10,14b-hexahydro-10-methyldibenzo[c,f]pyrido[1,2-a]azepin-2-yl]-2,2-difluoroacetamide (10: $R_8$=CN, $R_2$=$COCHF_2$; 13 mg, 34%). Data: (m/z)=382 (M+H)$^+$.

Example 7

Rel-N-[(2R,10R,14bR)-8-cyano-1,2,3,4,10,14b-hexahydro-10-methyldibenzo[c,f]pyrido[1,2-a]azepin-2-yl]methanesulfonamide (10: $R_8$=CN, $R_2$=$SO_2Me$)

This compound was prepared, in an analogous manner as described in Example 3, from 9 ($R_8$=CN) to afford 7, rel-N-[(2R,10R,14bR)-8-cyano-1,2,3,4,10,14b-hexahydro-10-methyldibenzo[c,f]pyrido[1,2-a]azepin-2-yl]methanesulfonamide (10: $R_8$=CN, $R_2$=$SO_2Me$; 13 mg, 34%). Data: (m/z)=382 (M+H)$^+$.

Example 8

Rel-N-[(2R,10R,14bR)-8-cyano-1,2,3,4,10,14b-hexahydro-10-methyldibenzo[c,f]pyrido[1,2-a]azepin-2-yl]ethanesulfonamide (10: $R_8$=CN, $R_2$=SO2Et)

This compound was prepared, in an analogous manner as described in Example 3, from 9 ($R_8$=CN) to afford rel-N-[(2R,10R,14bR)-8-cyano-1,2,3,4,10,14b-hexahydro-10-methyldibenzo[c,f]pyrido[1,2-a]azepin-2-yl]ethanesulfonamide (10: $R_8$=CN, $R_2$=$SO_2Et$; 12 mg, 30%). Data: (m/z)=396 (M+H)$^+$.

Example 9

Rel-N'-[(2R, 10R,14bR)-8-cyano-1,2,3,4,10,14b-hexahydro-10-methyldibenzo[c,f]pyrido[1,2-a]azepin-2-yl]-N,N-dimethylaminosulfamide (10: $R_8$=CN, $R_2$=$SO_2N(CH_3)_2$)

This compound was prepared, in an analogous manner as described in Example 3, from 9 ($R_8$=CN) to afford rel-N'-[(2R,10R,14bR)-8-cyano-1,2,3,4,10,14b-hexahydro-10-methyldibenzo[c,f]pyrido[1,2-a]azepin-2-yl]-N,N-dimethylaminosulfamide (10: $R_8$=CN, $R_2$=SO2N(CH3)$_2$; 12 mg, 29%). Data: (m/z)=411 (M+H)$^+$.

Example 10

Rel-N-[(2R,10R,14bR)-8-cyano-1,2,3,4,10,14b-hexahydro-10-methyldibenzo[c,f]pyrido[1,2-a]azepin-2-yl]-3,5-dimethylisoxazole-4-carboxamide (10: $R_8$=CN, $R_2$=$COC_5H_6NO$)

This compound was prepared, in an analogous manner as described in Example 3, from 9 ($R_8$=CN) to afford rel-N-[(2R,10R,14bR)-8-cyano-1,2,3,4,10,14b-hexahydro-10-methyldibenzo[c,f]pyrido[1,2-a]azepin-2-yl]-3,5-dimethylisoxazole-4-carboxamide (10: $R_8$=CN, $R_2$=$COC_5H_6NO$; 15 mg, 35%). Data: (m/z)=427 (M+H)$^+$.

Example 11

Rel-N-[(2R,10R,14bR)-8-acetyl-1,2,3,4,10,14b-hexahydro-10-methyldibenzo[c,f]pyrido[1,2-a]azepin-2-yl]-2,2,2-trifluoroacetamide (10: $R_8$=$COCH_3$, $R_2$=$COCF_3$)

A stirred solution of 10 ($R_8$=Br, $R_2$=$COCF_3$; 250 mg, 0.55 mmol) in toluene was charged with $PdCl_2(PPh_3)_2$ (8 mg, 0.011 mmol) and 1-ethoxyvinyltributyltin (587 μl, 1.73 mmol). The reaction mixture was stirred overnight under reflux. A HCl solution in $H_2O$ (2 N, 3 mL) was added and the reaction mixture was stirred for 10 minutes at room temperature. The reaction was quenched with a saturated $NaHCO_3$ solution in $H_2O$ and the product was extracted into ethyl acetate. The organic layer was washed with brine, dried ($Na_2SO_4$) and concentrated under reduced pressure. The crude product was purified by column chromatography on silica to afford rel-N-[(2R,10R,14bR)-8-acetyl-1,2,3,4,10,14b-hexahydro-10-methyldibenzo[c,f]pyrido[1,2-a]azepin-2-yl]-2,2,2-trifluoroacetamide (10: $R_8$=$COCH_3$, $R_2$=$COCF_3$; 150 mg, 65%). Data: (m/z)=417 (M+H)$^+$.

Example 12

Rel-N-[(2R,10R,14bR)-8-acetyl-1,2,3,4,10,14b-hexahydro-10-methyldibenzo[c,f]pyrido[1,2-a]azepin-2-yl]-4-methyl-1,2,3-thiadiazole-5-carboxamide (10: $R_8$=$COCH_3$, $R_2$=$COC_3H_3N_2S$)

This compound was prepared, in an analogous manner as described in Example 3, from 10 ($R_8$=$COCH_3$, $R_2$=$COCF_3$) to afford rel-N-[(2R,10R,14bR)-8-acetyl-1,2,3,4,10,14b-hexahydro-10-methyldibenzo[c,f]pyrido[1,2-a]azepin-2-yl]-4-methyl-1,2,3-thiadiazole-5-carboxamide (10: $R_8$=$COCH_3$, $R_2$=$COC_3H_3N_2S$; 27 mg, 54%). Data: (m/z)=447 (M+H)$^+$.

Example 13

Rel-2,2,2-trifluoro-N-[(2R,10R,14bR)-1,2,3,4,10, 14b-hexahydro-8-[1-(hydroxyimino)ethyl]-10-methyldibenzo[c,f]pyrido[1,2-a]azepin-2-yl]acetamide (10: $R_8$=C($CH_3$)NOH, $R_2$=$COCF_3$)

A stirred solution of 10 ($R_8$=$COCH_3$, $R_2$=$COCF_3$; 60 mg, 0.14 mmol) in EtOH was charged with hydroxylamine-.HCl (20 mg, 0.28 mmol) and pyridine (35 μl, 0.45 mmol). The reaction mixture was stirred at room temperature for 40 hours. The reaction was quenched with $H_2O$ and the product was extracted into ethyl acetate. The organics were washed with $H_2O$ and brine, dried ($Na_2SO4$) and concentrated under reduced pressure. The crude product was purified by column chromatography on silica. Freeze-drying from acetonitrile/$H_2O$ afforded rel-2,2,2-trifluoro-N-[(2R,10R,14bR)-1,2,3,4,10,14b-hexahydro-8-[1-(hydroxyimino)ethyl]-10-methyldibenzo[c,f]pyrido-[1,2-a]azepin-2-yl]acetamide (10: $R_8$=C($CH_3$)NOH, $R_2$=$COCF_3$; 50 mg, 80%). Data: (m/z)=432 (M+H)$^+$.

Example 14

Rel-2,2,2-trifluoro-N-[(2R,10R,14bR)-1,2,3,4,10, 14b-hexahydro-10-methyl-8-(pyridin-4-yl)dibenzo[c,f]pyrido[1,2-a]azepin-2-yl]acetamide (10: $R_8$=$C_5H_4N$, $R_2$=$COCF_3$)

To a stirred solution of 10 ($R_8$=Br, $R_2$=$COCF_3$; 67 mg, 0.148 mmol) in a mixture of dioxane (3 mL) and $H_2O$ (0.5 mL) $PdCl_2$ ($PPh_3$)$_2$ (6 mg, 8.8×10$^3$ mmol), $K_3PO_4$.$7H_2O$ (60 mg, 0.178 mmol), $AsPh_3$ (3 mg, 0.010 mmol) and 2,2-dimethylpropanediol cyclic ester pyridine-4-boronic acid (78 mg, 0.408 mmol) were added. The reaction mixture was stirred overnight under reflux. The reaction was quenched with a saturated $NaHCO_3$ solution in $H_2O$ and the product was extracted into DCM, dried ($Na_2SO4$) and concentrated under reduced pressure. The crude product was purified by column chromatography on silica affording rel-2,2,2-trifluoro-N-[(2R,10R,14bR)-1,2,3,4,10,14b-hexahydro-10-methyl-8-(pyridin-4-yl)dibenzo[c,f]pyrido-[1,2-a]azepin-2-yl]acetamide (10: $R_8$=C5H4N, $R_2$=$COCF_3$; 24 mg, 36%). Data: (m/z)=452 (M+H)$^+$.

Example 15

Rel-2,2-dichloro-N-[(2R,10R,14bR)-1,2,3,4,10,14b-hexahydro-10-methyl-8-(pyridin-4-yl)dibenzo[c,f]pyrido[1,2-a]azepin-2-yl]acetamide (10: $R_8$=$C_5H_4N$, $R_2$=$COCHCl_2$)

This compound was prepared, in an analogous manner as described in Example 3, from 10 ($R_8$=$C_5H_4N$, $R_2$=$COCF_3$) to afford rel-2,2-dichloro-N-[(2R,10R,14bR)-1,2,3,4,10,14b-hexahydro-10-methyl-8-(pyridin-4-yl)dibenzo[c,f]pyrido[1,2-a]azepin-2-yl]acetamide (10: $R_8$=$C_5H_4N$, $R_2$=$COCHCl_2$; 18 mg, 55%). Data: (m/z)=467 (M+H)$^+$.

Example 16

Rel-2-chloro-2,2-difluoro-N-[(2R,10R,14bR)-1,2,3, 4,10,14b-hexahydro-10-methyl-8-(pyridin-4-yl) dibenzo[c,f]pyrido[1,2-a]azepin-2-yl]acetamide (10: $R_8$=$C_5H_4N$, $R_2$=$COCF_2Cl$)

This compound was prepared, in an analogous manner as described in Example 3, from 9 ($R_8$=$C_5H_4N$) to afford rel-2-chloro-2,2-difluoro-N-[(2R,10R,14bR)-1,2,3,4,10,14b-hexahydro-10-methyl-8-(pyridin-4-yl)dibenzo[c,f]pyrido[1,2-a]azepin-2-yl]acetamide (10: $R_8$=$C_5H_4N$, $R_2$=$COCF_2Cl$; 20 mg, 61%). Data: (m/z)=468 (M+H)$^+$.

Example 17

Rel-N-[(2R,10R,14bR)-1,2,3,4,10,14b-hexahydro-10-methyl-8-(pyridin-4-yl)dibenzo[c,f]pyrido[1,2-a] azepin-2-yl]acetamide (10: $R_8$=$C_5H_4N$, $R_2$=$COCH_3$)

This compound was prepared, in an analogous manner as described in Example 3, from 9 ($R_8$=C5H4N) to afford rel-N-[(2R,10R,14bR)-1,2,3,4,10,14b-hexahydro-10-methyl-8-(pyridin-4-yl)dibenzo[c,f]pyrido[1,2-a]azepin-2-yl]acetamide (10: $R_8$=$C_5H_4N$, $R_2$=$COCH_3$; 7 mg, 26%). Data (m/z)=398 (M+H)$^+$.

Example 18

Rel-N-[(2R,10R,14bR)-1,2,3,4,10,14b-hexahydro-10-methyl-8-(pyridin-4-yl)dibenzo[c,f]pyrido[1,2-a] azepin-2-yl]isoxazole-5-carboxamide (10: $R_8$=$C_5H_4N$, $R_2$=$COC_3H_2NO$)

This compound was prepared, in an analogous manner as described in Example 3, from 9 ($R_8$=$C_5H_4N$) to afford rel-N-[(2R,10R,14bR)-1,2,3,4,10,14b-hexahydro-10-methyl-8-(pyridin-4-yl)dibenzo[c,f]pyrido[1,2-a]azepin-2-yl]isoxazole-5-carboxamide (10: $R_8$=$C_5H_4N$, $R_2$=$COC_3H_2NO$; 19 mg, 57%). Data: (m/z)=451 (M+H)$^+$.

Example 19

Rel-N-[(2R,10R, 14bR)-1,2,3,4,10,14b-hexahydro-10-methyl-8-(pyridin-4-yl)dibenzo[c,f]pyrido[1,2-a] azepin-2-yl]-5-methyl-isoxazole-3-carboxamide (10: $R_8$=$C_5H_4N$, $R_2$=$COC_4H_4NO$)

This compound was prepared, in an analogous manner as described in Example 3, from 9 ($R_8$=$C_5H_4N$) to afford rel-N-[(2R,10R,14bR)-1,2,3,4,10,14b-hexahydro-10-methyl-8-(pyridin-4-yl)dibenzo[c,f]pyrido[1,2-a]azepin-2-yl]-5-methyl-isoxazole-3-carboxamide (10: $R_8$=$C_5H_4N$, $R_2$=$COC_4H_4NO$; 22 mg, 67%). Data: (m/z)=465 (M+H)$^+$.

Example 20

Rel-N-[(2R,10R,14bR)-1,2,3,4,10,14b-hexahydro-10-methyl-8-(pyridin-4-yl)dibenzo[c,f]pyrido[1,2-a] azepin-2-yl]-4-methyl-1,2,3-thiadiazole-5-carboxamide (10: $R_8$=$C_5H_4N$, $R_2$=$COC_3H_3N_2S$)

This compound was prepared, in an analogous manner as described in Example 3, from 9 ($R_8$=$C_5H_4N$) to afford rel-N-[(2R,10R,14bR)-1,2,3,4,10,14b-hexahydro-10-methyl-8-(pyridin-4-yl)dibenzo[c,f]pyrido[1,2-a]azepin-2-yl]-4-methyl-1,2,3-thiadiazole-5-carboxamide (10: $R_8$=$C_5H_4N$, $R_2$=$COC_3H_3N_2S$; 20 mg, 59%). Data: (m/z)=482 (M+H)$^+$.

Example 21

Rel-N-[(2R,10R,14bR)-1,2,3,4,10,14b-hexahydro-10-methyl-8-(pyridin-4-yl)dibenzo[c,f]pyrido[1,2-a] azepin-2-yl]-2-thiophenacetamide (10: $R_8$=$C_5H_4N$, $R_2$=$COC_5H_5S$)

This compound was prepared, in an analogous manner as described in Example 3, from 9 ($R_8$=$C_5H_4N$) to afford rel- N-[(2R,10R,14bR)-1,2,3,4,10,14b-hexahydro-10-methyl-8-(pyridin-4-yl)dibenzo[c,f]pyrido[1,2-a]azepin-2-yl]-2-thiophenacetamide (10: $R_8=C_5H_4N$, $R_2=COC_5H_5S$) 21 mg, 62%). Data: (m/z)=480 (M+H)$^+$.

Example 22

Rel-N-[(2R,10R,14bR)-1,2,3,4,10,14b-hexahydro-10-methyl-8-(pyridin-4-yl)dibenzo[c,f]pyrido[1,2-a]azepin-2-yl]methanesulfonamide (10: $R_8=C_5H_4N$ 4-pyridine, $R_2=SO_2Me$)

This compound was prepared, in an analogous manner as described in Example 3, from 9 ($R_8=C_5H_4N$) to afford rel-N-[(2R,10R,14bR)-1,2,3,4,10,14b-hexahydro-10-methyl-8-(pyridin-4-yl)dibenzo[c,f]pyrido[1,2-a]azepin-2-yl]methanesulfonamide (10: $R_8=C_5H_4N$, $R_2=SO_2Me$; 19 mg, 62%). Data: (m/z)=434 (M+H)$^+$.

Example 23

Rel-N-[(2R,10R,14bR)-1,2,3,4,10,14b-hexahydro-10-methyl-8-(pyridin-4-yl)dibenzo[c,f]pyrido[1,2-a]azepin-2-yl]ethanesulfonamide (10: $R_8=C_5H_4N$, $R_2=SO_2Et$)

This compound was prepared, in an analogous manner as described in Example 3, from 9 ($R_8=C_5H_4N$) to afford rel-N-[(2R,10R,14bR)-1,2,3,4,10,14b-hexahydro-10-methyl-8-(pyridin-4-yl)dibenzo[c,f]pyrido[1,2-a]azepin-2-yl]ethanesulfonamide (10: $R_8=C_5H_4N$, $R_2=SO_2Et$; 10 mg, 32%). Data: (m/z)=448 (M+H)$^+$.

Example 24

Rel-N'-[(2R,10R,14bR)-1,2,3,4,10,14b-hexahydro-10-methyl-8-(pyridin-4-yl)dibenzo[c,f]pyrido[1,2-a]azepin-2-yl]-N,N-dimethylaminosulfamide (10: $R_8=C_5H_4N$, $R_2=SO_2N(CH_3)_2$)

This compound was prepared, in an analogous manner as described in Example 3, from 9 ($R_8=C_5H_4N$) to afford rel-N'-[(2R,10R,14bR)-1,2,3,4,10,14b-hexahydro-10-methyl-8-(pyridin-4-yl)dibenzo[c,f]pyrido[1,2-a]azepin-2-yl]-N,N-dimethylaminosulfamide (10: $R_8=C_5H_4N$, $R_2=SO_2N(CH_3)_2$; 14 mg, 42%). Data: (m/z)=463 (M+H)$^+$.

Example 25

Rel-2,2-difluoro-N-[(2R,10R,14bR)-1,2,3,4,10,14b-hexahydro-10-methyl-8-(pyridin-4-yl)dibenzo[c,f]pyrido[1,2-a]azepin-2-yl]acetamide (10: $R_8=C_5H_4N$, $R_2=COCHF_2$)

This compound was prepared, in an analogous manner as described in Example 6, from 9 ($R_8=C_5H_4N$) to afford rel-2,2-difluoro-N-[(2R,10R,14bR)-1,2,3,4,10,14b-hexahydro-10-methyl-8-(pyridin-4-yl)dibenzo[c,f]pyrido[1,2-a]azepin-2-yl]acetamide to (10: $R_8=C_5H_4N$, $R_2=COCHF_2$; 15 mg, 50%). Data: (m/z)=434 (M+H)$^+$.

Example 26

Rel-4-amino-N-[(2R,10R,14bR)-1,2,3,4,10,14b-hexahydro-10-methyl-8-(pyridin-4-yl)dibenzo[c,f]pyrido[1,2-a]azepin-2-yl]-1,2,5-oxadiazole-3-carboxamide (10: $R_8=C_5H_4N$, $R_2=COC_2H_2N_3O$)

This compound was prepared, in an analogous manner as described in Example 6, from 9 ($R_8=C_5H_4N$) to afford rel-4-amino-N-[(2R,10R,14bR)-1,2,3,4,10,14b-hexahydro-10-methyl-8-(pyridin-4-yl)dibenzo[c,f]pyrido[1,2-a]azepin-2-yl]-1,2,5-oxadiazole-3-carboxamide (10: $R_8=C_5H_4N$, $R_2=COC_2H_2N_3O$; 23 mg, 70%). Data: (m/z)=467 (M+H)$^+$.

Example 27

Rel-2,2,2-trifluoro-N-[(2R,10R,14bR)-1,2,3,4,10,14b-hexahydro-10-methyl-8-(pyrimidin-2-yl)dibenzo[c,f]pyrido[1,2-a]azepin-2-yl]acetamide (10: $R_8=C_4H_3N_2$, $R_2=COCF_3$)

To a stirred solution of 10 ($R_8=Br$, $R_2=COCF_3$; 100 mg, 0.22 mmol) in dioxane tributylstannylpyrimidine (98 mg, 0.26 mmol), CsF (72 mg, 0.473 mmol), $Pd_2$ (dba)$_3$ (palladium dibenzylideneacetone, 6 mg, 6.6 μmol) and P(tBu)$_3$ (10% solution in hexane, 26 μmol) were added. The reaction mixture was stirred overnight under reflux. The reaction was quenched with $H_2O$ and the organics were extracted into ethyl acetate. The organic layer was washed with brine, dried (Na$_2$SO$_4$) and concentrated under reduced pressure. The crude product was purified by column chromatography on silica, followed by preparative HPLC. Freeze-drying from acetonitrile/$H_2O$ afforded rel-2,2,2-trifluoro-N-[(2R, 10R, 14bR)-1,2,3,4,10,14b-hexahydro-10-methyl-8-(pyrimidin-2-yl]dibenzo[c,f]pyrido[1,2-a]azepin-2-yl]acetamide (10: $R_8=C_4H_3N_2$, $R_2=COCF_3$; 31 mg, 31%). Data: (m/z)=453 (M+H)$^+$.

Example 28

Rel-N-[(2R,10R,14bR)-1,2,3,4,10,14b-hexahydro-10-methyl-8-(pyrimidin-2-yl)dibenzo[c,f]pyrido[1,2-a]azepin-2-yl]-4-methyl-1,2,3-thiadiazole-5-carboxamide (10: $R_8=C_4H_3N_2$, $R_2=COC_3H_3N_2S$)

This compound was prepared, in an analogous manner as described in Example 3, from 10 ($R_8=C_4H_3N_2$, $R_2=COCF_3$) to afford rel-N-[(2R,10R,14bR)-1,2,3,4,10,14b-hexahydro-10-methyl-8-(pyrimidin-2-yl)dibenzo[c,f]pyrido[1,2-a]azepin-2-yl]-4-methyl-1,2,3-thiadiazole-5-carboxamide (10: $R_8=C_4H_3N_2$, $R_2=COC_3H_3N_2S$; 14 mg, 47%). Data: (m/z)=483 (M+H)$^+$.

Example 29

Rel-2,2,2-trifluoro-N-[(2R,10R,14bR)-1,2,3,4,10,14b-hexahydro-10-methyl-8-(pyrazin-2-yl)dibenzo[c,f]pyrido[1,2-a]azepin-2-yl]acetamide (10: $R_8=C_4H_3N_2$, $R_2=COCF_3$)

This compound was prepared, in an analogous manner as described in Example 27, from 10 ($R_8=Br$, $R_2=COCF_3$) to afford rel-2,2,2-trifluoro-N-[(2R,10R,14bR)-1,2,3,4,10,14b-hexahydro-10-methyl-8-(pyrazin-2-yl)dibenzo[c,f]pyrido[1,2-a]azepin-2-yl]acetamide (10: $R_8=C_4H_3N_2$, $R_2=COCF_3$; 24 mg, 24%). Data: (m/z)=453 (M+H)$^+$.

Example 30

Methyl Rel-(2R,10R,14bR)-1,2,3,4,10,14b-hexahydro-10-methyl-2-(2,2,2-trifluoroacetylamino)dibenzo[c,f]pyrido[1,2-a]azepine-8-carboxylate (10: $R_8=COOCH_3$, $R_2=COCF_3$)

To a solution of 10 ($R_8=CN$, $R_2=COCF_3$; 400 mg, 1 mmol) in EtOH (20 mL) a 6 N KOH solution in $H_2O$ (8.5 mL)

was added. The mixture was heated in the microwave to 120° C. (175 Watt) for 3 hours. Reaction mixture was neutralized with a 2N HCl solution in $H_2O$. The reaction mixture was concentrated under reduced pressure and coevaporated with toluene.

The residue was taken up in MeOH (30 mL) and triethylamine (277 µl, 2 mmol) and ethyl trifluoroacetate (597 µl, 5 mmol) were added. The reaction mixture was stirred overnight at 55° C. and then concentrated under reduced pressure. The crude product was purified by column chromatography on silica to afford (10: $R_8$=COOH, $R_2$=COCF$_3$; 331 mg, 79%).

To a stirred solution of 10 ($R_8$=COOH, $R_2$=COCF$_3$; 30 mg, 0.072 mmol) in methanol (2 mL) at 0° C., thionylchloride (300 µl, 3.46 mmol) was added. The reaction mixture was stirred overnight at room temperature. The reaction mixture was quenched with a saturated NaHCO$_3$ solution in $H_2O$ and the product was extracted into ethyl acetate. The organics were washed with brine, dried (Na$_2$SO$_4$) and concentrated under reduced pressure. The crude product was purified by column chromatography on silica (Heptane:Ethyl acetate=8:2). Freeze-drying from acetonitrile/$H_2O$ afforded methyl rel-(2R,10R,14bR)-1,2,3,4,10,14b-hexahydro-10-methyl-2-(2,2,2-trifluoroacetylamino)dibenzo[c,f]pyrido[1,2-a]azepine-8-carboxylate (10: $R_8$=COOCH$_3$, $R_2$=COCF$_3$; 10.3 mg, 33%). Data: (m/z)=433 (M+H)$^+$.

Example 31

Ethyl Rel-(2R,10R,14bR)-1,2,3,4,10,14b-hexahydro-10-methyl2-(2,2,2-trifluoroacetylamino)dibenzo[c,f]pyrido[1,2-a]azepine-8-carboxylate (10: $R_8$=COOCH$_2$CH$_3$, $R_2$=COCF$_3$)

This compound was prepared, in an analogous manner as described in Example 30, from 10 ($R_8$=COOH, $R_2$=COCF$_3$) to afford ethyl rel-(2R,10R,14bR)-1,2,3,4,10,14b-hexahydro-10-methyl-2-(2,2,2-trifluoroacetylamino) dibenzo[c,f]pyrido[1,2-a]azepine-8-carboxylate (10: $R_8$=COOCH$_2$CH$_3$, $R_2$=COCF$_3$; 18.9 mg, 59%). Data: (m/z)=447 (M+H)$^+$.

Example 32

Propyl Rel-(2R,10R,14bR)-1,2,3,4,10,14b-hexahydro-10-methyl 2-(2,2,2-trifluoroacetylamino)dibenzo[c,f]pyrido[1,2-a]azepine-8-carboxylate (10: $R_8$=COO(CH$_2$)$_2$CH$_3$, $R_2$=COCF$_3$)

This compound was prepared, in an analogous manner as described in Example 30, from 10 ($R_8$=COOH, $R_2$=COCF$_3$) to afford propyl rel-(2R,10R,14bR)-1,2,3,4,10,14b-hexahydro-10-methyl 2-(2,2,2-trifluoroacetylamino) dibenzo-[c,f]pyrido[1,2-a]azepine-8-carboxylate (10: $R_8$=COO(CH$_2$)$_2$CH$_3$, $R_2$=COCF$_3$; 10.3 mg, 33 %). Data: (m/z)=461 (M+H)$^+$.

Example 33

Rel-(2R,10R,14bR)-1,2,3,4,10,14b-hexahydro-10-methyl-N-phenyl-2-(2,2,2-trifluoroacetylamino) dibenzo[c,f]pyrido[1,2-a]azepine-8-carboxamide (10: $R_8$=CONH(C$_6$H$_5$), $R_2$=COCF$_3$)

To a stirred solution of 10 ($R_8$=COOH, $R_2$=COCF$_3$; 40 mg, 0.096 mmol) in DMF, TBTU (46 mg, 0.144 mmol) and DIPEA (84 µl, 0.48 mmol) were added. Then aniline (10 µl, 0.11 mmol) was added and the reaction mixture was stirred for 40 hours at room temperature. The reaction was quenched with $H_2O$ and the organics were extracted into DCM. The organic layer was dried over a separation filter and concentrated under reduced pressure. The crude product was purified by preparative HPLC, this afforded rel-(2R,10R,14bR)-1,2,3,4,10,14b-hexahydro-10-methyl-N-phenyl-2-(2,2,2-trifluoroacetylamino)dibenzo[c,f]pyrido[1,2-a]azepine-8-carboxamide (10: $R_8$=CONH(C$_6$H$_5$), $R_2$=COCF$_3$; 27.3 mg, 58%). Data: (m/z)=494 (M+H)$^+$.

Example 34

Rel-(2R,10R,14bR)-1,2,3,4,10,14b-hexahydro-10-methyl-N-(pyridin-4-yl)-2-(2,2,2-trifluoroacetylamino)dibenzo[c,f]pyrido[1,2-a]azepine-8-carboxamide (10: $R_8$=CONH(C$_5$H$_4$N), $R_2$=COCF$_3$)

This compound was prepared, in an analogous manner as described in Example 33, from 10 ($R_8$=COOH, $R_2$=COCF$_3$) to afford rel-(2R,10R,14bR)-1,2,3,4,10,14b-hexahydro-10-methyl-N-(pyridin-4-yl)-2-(2,2,2-trifluoroacetylamino)dibenzo[c,f]-pyrido[1,2-a]azepine-8-carboxamide (10: $R_8$=CONH(C$_5$H$_4$N), $R_2$=COCF$_3$; 17.5 mg, 37%). Data: (m/z)=495 (M+H)$^+$.)=495 (M+H)$^+$.

Example 35

Rel-(2R,10R,14bR)-1,2,3,4,10,14b-hexahydro-N-(2-methoxypyrimidin-5-yl)-10-methyl-2-(2,2,2-trifluoroacetylamino)dibenzo[c,f]pyrido[1,2-a]azepine-8-carboxamide (10: $R_8$=CONH(C$_6$H$_6$NO), $R_2$=COCF$_3$)

This compound was prepared, in an analogous manner as described in Example 33, from 10 ($R_8$=COOH, $R_2$=COCF3) to rel-(2R,10R,14bR)-1,2,3,4,10,14b-hexahydro-N-(2-methoxypyrimidin-5-yl)-10-methyl-2-(2,2,2-trifluoroacetylamino)dibenzo-[c,f]pyrido[1,2-a]azepine-8-carboxamide (10: $R_8$=CONH(C$_6$H$_6$NO), $R_2$=COCF$_3$; 35.5 mg, 71%). Data: (m/z)=525 (M+H)$^+$.

Example 36

Rel-(2R,10R,14bR)-1,2,3,4,10,14b-hexahydro-N-(2-methoxyphenyl)-10-methyl-2-(2,2,2-trifluoroacetylamino)-dibenzo[c,f]pyrido[1,2-a]azepine-8-carboxamide (10: $R_8$=CONH(C$_7$H$_7$O), $R_2$=COCF$_3$)

This compound was prepared, in an analogous manner as described in Example 33, from 10 ($R_8$=COOH, $R_2$=COCF$_3$) to rel-(2R,10R,14bR)-1,2,3,4,10,14b-hexahydro-N-(2-methoxyphenyl)-10-methyl-2-(2,2,2-trifluoroacetylamino)-dibenzo[c,f]-pyrido[1,2-a]azepine-8-carboxamide (10: $R_8$=CONHC$_7$H$_7$O, $R_2$=COCF$_3$; 30.3 mg, 61%). Data: (m/z)=524 (M+H)$^+$.

Example 37

Rel-2,2,2-trifluoro-N-[(2R,10R,14bR)-1,2,3,4,10,14b-hexahydro-10-methyl-8-(2-methyltetrazol-5-yl) dibenzo[c,f]pyrido[1,2-a]azepin-2-yl]acetamide (10: $R_8$=C$_2$N$_4$H$_3$, $R_2$=COCF$_3$)

To a solution of 10 ($R_8$=CN, $R_2$=COCF$_3$; 210 mg, 0.53 mmol) in DME (3 mL), trimethylsilylazide (278 µl, 2.12 mmol) and dibutyltinoxide (52 mg, 0.21 mmol) were added.

The mixture was heated in the microwave to 160° C. (300 Watt) for 45 min. The reaction mixture was quenched with 0.2 N NaOH and washed with ethyl acetate. Then the basic water-layer was acidified with 2 N HCl and extracted into ethyl acetate. The organic layer was washed with $H_2O$ and brine, dried ($Na_2SO_4$) and concentrated under reduced pressure to afford (10, $R_8=CN_4H$, $R_2=COCF_3$; 208 mg, 89%). Data: (m/z)=443 (M+H)$^+$.

To a solution of 10 ($R_8=CN_4H$, $R_2=COCF_3$; 200 mg, 0.45 mmol) in acetone/DMF (1/1 20 mL) $Na_2CO_3$ (72 mg, 0.68 mmol) was added followed by MeI (280 µl, 4.5 mmol). The reaction mixture was stirred for 3 hours at room temperature. The reaction was quenched with 2N HCl and extracted into ethyl acetate. The organic layer was washed with $H_2O$ and brine, dried ($Na_2SO_4$) and concentrated under reduced pressure. The crude product was purified by column chromatography on silica (Heptane:Ethyl acetate=6:4) to afford rel-2,2,2-trifluoro-N-[(2R,10R,14bR)-1,2,3,4,10,14b-hexahydro-10-methyl-8-(2-methyltetrazol-5-yl)dibenzo[c,f]pyrido[1,2-a]azepin-2-yl]acetamide (10, $R_8=C_2N_4H_3$, $R_2=COCF_3$; 99 mg 48%). Data: (m/z)=457 (M+H)$^+$.

Example 38

Rel-2-chloro-2,2-difluoro-N-[(2R,10R,14bR)-1,2,3, 4,10,14b-hexahydro-10-methyl-8-(2-methyltetrazol-5-yl)dibenzo[c,f]pyrido[1,2-a]azepin-2-yl]acetamide (10: $R_8=C_2N_4H_3$, $R_2=COCClF_2$)

This compound was prepared, in an analogous manner as described in Example 3, from 10 ($R_8=C_2N_4H_3$, $R_2=COCF_3$) to afford rel-2-chloro-2,2-difluoro-N-[(2R, 10R,14bR)-1,2,3,4,10,14b-hexahydro-10-methyl-8-(2-methyltetrazol-5-yl)dibenzo[c,f]pyrido[1,2-a]azepin-2-yl]acetamide (10: $R_8=C_2N_4H_3$, $R_2=COCClF_2$; 24 mg, 73%). Data: (m/z)=473 (M+H)$^+$.

Example 39

Rel-N-[(2R,10R,14bR)-1,2,3,4,10,14b-hexahydro-10-methyl-8-(2-methyltetrazol-5-yl)dibenzo[c,f] pyrido[1,2-a]azepin-2-yl]-4-methyl-1,2,3-thiadiazole-5-carboxamide (10: $R_8=C_2N_4H_3$, $R_2=COC_3H_3N_2S$)

This compound was prepared, in an analogous manner as described in Example 3, from 10 ($R_8=C_2N_4H_3$, $R_2=COCF_3$) to afford rel-N-[(2R,10R,14bR)-1,2,3,4,10, 14b-hexahydro-10-methyl-8-(2-methyltetrazol-5-yl) dibenzo[c,f]pyrido[1,2-a]azepin-2-yl]-4-methyl-1,2,3-thiadiazole-5-carboxamide (10: $R_8=C_2N_4H_3$, $R_2=COC_3H_3N_2S$; 17 mg, 50%). Data: (m/z)=487 (M+H)$^+$.

Example 40

Rel-2,2,2-trifluoro-N-[(2R,10R,14bR)-1,2,3,4,10, 14b-hexahydro-10-methyl-8-(pyrimidin-4-yl) dibenzo[c,f]pyrido[1,2-a]azepin-2-yl]acetamide (10: $R_8=C_4N_2H_3$, $R_2=COCF_3$)

A solution of 10 ($R_8=Br$, $R_2=COCF_3$; 1.9 g, 4.19 mmol), KOAc (1.23 g, 12.6 mmol) and bispinacolatoboron (1.17 g, 4.61 mmol) in DMF (60 mL) was degassed by bubbling nitrogen through for 15 minutes. $PdCl_2$ (dppf)$_2$ ([1,1' Bis (diphenylphosphino)fenocene]dichloropalladium(II); 103 mg, 0.13 mmol) was added and the reaction mixture was stirred overnight at 80° C. The reaction was quenched with $H_2O$ and the product was extracted into ethyl acetate. The organic layer was washed with brine, dried ($Na_2SO_4$) and concentrated under reduced pressure. The crude product was purified by column chromatography on silica (Heptane:Ethyl acetate=85:15) to afford 10 ($R_8=C_6H_{12}BO_2$, $R_2=COCF_3$; 1.06 g, 51%). Data: (m/z)=501 (M+H)$^+$.

To a stirred solution of 10 ($R_8=C_6H_{12}BO_2$, $R_2=COCF_3$; 1.12 g, 2.24 mmol) in a mixture of dioxane (42 mL) and $H_2O$ (7 mL) $PdCl_2$ (PPh$_3$)$_2$ (47 mg, 0.067 mmol), $K_3PO_4.7H_2O$ (910 mg, 2.69 mmol), AsPh$_3$ (47 mg, 0.154 mmol) and 4,6-dichloropyrimidine (918 mg, 6.16 mmol) were added. The reaction mixture was stirred overnight at 100° C. The reaction was quenched with a saturated $NaHCO_3$ solution in $H_2O$ and the product was extracted into ethyl acetate, washed with brine, dried ($Na_2SO_4$) and concentrated under reduced pressure. The crude product was purified by column chromatography on silica affording (10: $R_8=C_4H_2N_2Cl$, $R_2=COCF_3$; 0.64g, 63%). Data: (m/z)=487 (M+H)$^+$.

To a stirred solution of 10 ($R_8=C_4H_2N_2Cl$, $R_2=COCF_3$; 614 mg, 1.26 mmol) in THF (50 mL) and ammonia (22 mL), zinc (2.17 g 33.2 mmol) was added. The reaction mixture was stirred for 5 hours under reflux. The reaction was quenched with a saturated $NaHCO_3$ solution in $H_2O$ and filtered over decalite. The product was extracted into ethyl acetate, washed with brine, dried ($Na_2SO_4$) and concentrated under reduced pressure. The crude product was purified by column chromatography on silica affording rel-2,2,2-trifluoro-N-[(2R,10R, 14bR)-1,2,3,4,10,14b-hexahydro-10-methyl-8-(pyrimidin-4-yl)dibenzo[c,f]pyrido[1,2-a]azepin-2-yl]acetamide (10: $R_8=C_4H_3N_2$, $R_2=COCF_3$; 485 mg, 85%). Data: (m/z)=453 (M+H)$^+$.

Example 41

Rel-2,2,2-trifluoro-N-[(2R,10R,14bR)-1,2,3,4,10, 14b-hexahydro-10-methyl-8-(pyridin-2-yl)dibenzo[c, f]pyrido[1,2-a]azepin-2-yl]acetamide (10: $R_8=C_5H_4N$, $R_2=COCF_3$)

To a stirred solution of 10 $R_8=C_6H_{12}BO_2$, $R_2=COCF_3$; 50 mg, 0.10 mmol) in a mixture of dioxane (3 mL) and $H_2O$ (0.5 mL) $PdCl_2$ (PPh$_3$)$_2$ (6 mg, 8.55 µmol), $K_3PO_4.7H_2O$ (40 mg, 0.12 mmol), AsPh$_3$ (6 mg, 19.6 µmol) and 2-bromopyridine (26.3 µl, 0.28 mmol) were added. The reaction mixture was stirred overnight at 100° C. The reaction was quenched with a saturated $NaHCO_3$ solution in $H_2O$ and the product was extracted into ethyl acetate, washed with brine, dried ($Na_2SO_4$) and concentrated under reduced pressure. The crude product was purified by column chromatography on silica followed by preparative HPLC to afford pure rel-2,2,2-trifluoro-N-[(2R,10R,14bR)-1,2,3,4,10,14b-hexahydro-10-methyl-8-(pyridin-2-yl)dibenzo[c,f]pyrido[1,2-a]azepin-2-yl]acetamide. (10: $R_8=C_5H_4N$, $R_2=COCF_3$; 8 mg, 18%). Data: (m/z)=452 (M+H)$^+$.

Example 42

Rel-N-[(2R,10R,14bR)-1,2,3,4,10,14b-hexahydro-10-methyl-8-(pyrimidin-4-yl)dibenzo[c,f]pyrido[1,2-a]azepin-2-yl]-4-methyl-1,2,3-thiadiazole-5-carboxamide (10: $R_8=C_4H_3N_2$, $R_2=COC_3H_3N_2S$)

This compound was prepared, in an analogous manner as described in Example 3, from 10 ($R_8=C_4H_3N_2$, $R_2=COCF_3$) to afford rel-N-[(2R,10R,14bR)-1,2,3,4,10, 14b-hexahydro-10-methyl-8-(pyrimidin-4-yl)dibenzo[c,f] pyrido[1,2-a]azepin-2-yl]-4-methyl-1,2,3-thiadiazole-5-carboxamide (10: $R_8$=$C_4H_3N_2$, $R_2$=$COC_3H_3N_2S$; 20 mg, 62%). Data: (m/z)=483 (M+H)$^+$.

Example 43

Rel-2,2-chloro-N-[(2R,10R,14bR)-1,2,3,4,10,14b-hexahydro-10-methyl-8-(pyrimidin-4-yl]dibenzo[c,f]pyrido[1,2-a]azepin-2-yl]acetamide (10: $R_8$=$C_4H_3N_2$, $R_2$=COCHCl$_2$)

This compound was prepared, in an analogous manner as described in Example 3, from 10 ($R_8$=$C_4H_3N_2$, $R_2$=COCF$_3$) to afford rel-2,2-chloro-N-[(2R,10R,14bR)-1,2,3,4,10,14b-hexahydro-10-methyl-8-(pyrimidin-4-yl)dibenzo[c,f]pyrido[1,2-a]azepin-2-yl]acetamide (10: $R_8$=$C_4H_3N_2$, $R_2$=COCHCl$_2$; 17 mg, 53%). Data: (m/z)=468 (M+H)$^+$.

Example 44

Rel-N-[(2R,10R,14bR)-1,2,3,4,10,14b-hexahydro-10-methyl-8-(pyrimidin-4-yl)dibenzo[c,f]pyrido[1,2-a]azepin-2-yl]methanesulfonamide (10: $R_8$=$C_4H_3N_2$, $R_2$=COSO$_2$CH$_3$)

This compound was prepared, in an analogous manner as described in Example 3, from 10 ($R_8$=$C_4H_3N_2$, $R_2$=COCF$_3$) to afford rel-N-[(2R,10R,14bR)-1,2,3,4,10,14b-hexahydro-10-methyl-8-(pyrimidin-4-yl)dibenzo[c,f]pyrido[1,2-a]azepin-2-yl]methanesulfonamide (10: $R_8$=$C_4H_3N_2$, $R_2$=COSO$_2$CH$_3$; 22 mg, 72%). Data: (m/z)=435 (M+H)$^+$.

Example 45

Rel-2-chloro-2,2-difluoro-N-[(2R,10R,14bR)-1,2,3,4,10,14b-hexahydro-10-methyl-8-(pyrimidin-4-yl)dibenzo[c,f]pyrido[1,2-a]azepin-2-yl]acetamide (10: $R_8$=$C_4H_3N_2$, $R_2$=COCClF$_2$)

This compound was prepared, in an analogous manner as described in Example 3, from 10 ($R_8$=$C_4H_3N_2$, $R_2$COCF$_3$) to afford rel-2-chloro-2,2-difluoro-N-[(2R,10R,14bR)-1,2,3,4,10,14b-hexahydro-10-methyl-8-(pyrimidin-4-yl)dibenzo[c,f]pyrido[1,2-a]azepin-2-yl]acetamide (10: $R_8$=$C_4H_3N_2$, $R_2$=COCClF$_2$; 23 mg, 70%). Data: (m/z)=469 (M+H)$^+$.

Example 46

Rel-5-amino-N-[(2R,10R,14bR)-1,2,3,4,10,14b-hexahydro-10-methyl-8-(pyrimidin-4-yl)dibenzo[c,f]pyrido[1,2-a]azepin-2-yl]-1,2,5-oxadiazole-4-carboxamide (10: $R_8$=$C_4H_3N_2$, $R_2$=COCH$_2$N$_3$O)

This compound was prepared, in an analogous manner as described in Example 6, from 10 ($R_8$=$C_4H_3N_2$, $R_2$=COCF$_3$) to afford rel-5-amino-N-[(2R,10R,14bR)-1,2,3,4,10,14b-hexahydro-10-methyl-8-(pyrimidin-4-yl)dibenzo[c,f]pyrido[1,2-a]azepin-2-yl]-1,2,5-oxadiazole-4-carboxamide (10: $R_8$=$C_4H_3N_2$, $R_2$=COCH$_2$N$_3$O; 22 mg, 68%). Data: (m/z)=468 (M+H)$^+$.

Example 47

Rel-2,2,2-trifluoro-N-[(2R,4S,10R,14bR)-1,2,3,4,10,14b-hexahydro-4,10-dimethyldibenzo[c,f]pyrido[1,2-a]azepin-2-yl]acetamide (10: $R_2$=COCF$_3$, $R_4$=CH$_3$)

To a stirred solution of 9 ($R_4$=CH$_3$; 34 mg, 0.12 mmol) (prepared in an analogous manner as described above in Example 1); in MeOH (5 mL), triethylamine (81 µl, 0.58 mmol) and ethyltrifluoroacetate (69 µl, 0.58 mmol) were added and the reaction mixture was heated to 50° C. and held for 5 hours. The reaction mixture was concentrated under reduced pressure then purified by column chromatography on silica to afford rel-2,2,2-trifluoro-N-[(2R,4S,10R,14bR)-1,2,3,4,10,14b-hexahydro-4,10-dimethyldibenzo[c,f]pyrido[1,2-a]azepin-2-yl]acetamide (10: $R_2$=COCF$_3$, $R_4$=CH$_3$). (24 mg, 53%). Data: (m/z)=389 (M+H)$^+$.

Example 48

Rel-N-[(2R,10R,14bR)-8-cyano-1,2,3,4,10,14b-hexahydro-10-methyldibenzo[c,f]pyrido[1,2-a]azepin-2-yl]-N'-methyl-N'-methoxyurea (10, $R_8$=CN, $R_2$=CON(CH$_3$)O(CH$_3$))

To a stirred solution of 9 ($R_8$=CH; 75 mg, 0.248 mmol) in ethyl acetate (4 mL), a catalytic amount of activated carbon and trichloromethylchloroformate (35 mL, 0.298 mmol) were added. The reaction mixture was heated to reflux temperature. After 5 hours the reaction mixture was filtered over decalite and concentrated under reduced pressure to give 9 ($R_8$=CN, $R_2$=CNO).

To a stirred solution of isocyanate 9 ($R_8$=CH, $R_2$=CNO) in ethyl acetate (10 mL) Et$_3$N (173 mL, 1.25 mmol) and N,O-dimethylhydroxylamine.HCl (121 mg 1.25 mmol) were added and the reaction was stirred overnight at 50° C. Then reaction was quenched with a saturated NaHCO$_3$ solution in H$_2$O and the product was extracted into ethyl acetate. The organics were washed with H$_2$O, a saturated NaCl solution in H$_2$O, dried (Na$_2$SO$_4$) and concentrated under reduced pressure. The crude produce was purified by column chromatography on silica, followed by preparative HPLC. Freeze-drying from acetonitrile/H$_2$O afforded rel-N-[(2R,10R,14bR)-8-cyano-1,2,3,4,10,14b-hexahydro-10-methyldibenzo[c,f]pyrido[1,2-a]azepin-2-yl]-N'-methyl-N'-methoxyurea (10, $R_8$=CN, $R_2$=CON(CH$_3$)O(CH$_3$); 30 mg, 31%). Data: (m/z)=391 (M+H)$^+$.

Example 49

Rel-N-[(2R,10R,14bR)-8-cyano-1,2,3,4,10,14b-hexahydro-10-methyldibenzo[c,f]pyrido[1,2-a]azepin-2-yl]-2-hydroxyacetamide (10: $R_8$=CN, $R_2$=CDCH$_2$OH)

A stirred solution of 9 ($R_8$=CN; 25 mg, 0.0825 mmol) and triethylamine (14 mL, 0.099 mmol) in DCM (2 mL) was cooled to 0° C. Acetoxyacetylchloride (11 mL, 0.099 mmol) was added and the reaction was stirred at room temperature for 2 hours. The reaction was quenched with a saturated NaHCO$_3$ solution in H$_2$O and the product was extracted into DCM. The organics were dried and concentrated under reduced pressure. The crude product was purified by column chromatography on silica to give 10 ($R_8$=CN, $R_2$=COCH$_2$OC(O)CH$_3$; 30 mg, 90%). Data: (m/z)=404 (M+H)$^+$.

To a stirred solution of 10 ($R_8$=CN, $R_2$=COCH$_2$OC(O)CH$_3$; 30 mg, 0.075 mmol) in MeOH (3 mL) KOH (42 mg, 0.75 mmol) in H$_2$O (1.5 mL) was added and the reaction mixture was stirred at room temperature for 15 minutes. The reaction mixture was poured into H$_2$O and the product was extracted into ethyl acetate. The organics were washed with H$_2$O and brine, dried (Na$_2$SO$_4$) and concentrated under reduced pressure. The crude product was purified by column chromatography on silica, followed by preparative HPLC. Freeze-drying from acetonitrile/H$_2$O afforded rel-N-[(2R,10R,14bR)-8-cyano-1,2,3,4,10,14b-hexahydro-10-methyldibenzo[c,f]pyrido[1,2-a]azepin-2-yl]-2-hydroxyacetamide (10, $R_8$=CN, $R_2$=COCH$_2$OH; 7.5 mg, 28%). Data: (m/z)=362 (M+H)$^+$.

Example 50

Rel-(2R,10R,14bR)-2-[(N,N-dimethylaminocarbonyl)amino]-1,2,3,4,10,14b-hexahydro-10-methyl-N-phenyldibenzo[c,f]pyrido[1,2-a]azepine-8-carboxamide (10: $R_8$=CONH(C$_6$H$_5$), $R_2$=CON(CH$_3$)$_2$)

This compound was prepared, in an analogous manner as described in Example 3, from 10 ($R_8$=CONH(C$_6$H$_5$), $R_2$=COCF$_3$) to afford rel-(2R,10R,14bR)-2-[(N,N-dimethylaminocarbonyl)amino]-1,2,3,4,10,14b-hexahydro-10-methyl-N-phenyldibenzo[c,f]pyrido[1,2-a]azepine-8-carboxamide (10: $R_8$=CONH(C$_6$H$_5$), $R_2$=CON(CH$_3$)$_2$; 7.4 mg, 30%). Data: (m/z)=469(M+H)$^+$.

Example 51

Rel-2,2,2-trifluoro-N-[(2R,10R,14bR)-8-[4,5-dihydrooxazol-2-yl]-1,2,3,4,10,14b-hexahydro-10-methyldibenzo[c,f]pyrido[1,2-a]azepin-2-yl]acetamide (10: $R_8$=C$_3$H$_4$NO, $R_2$=COCF$_3$)

To a stirred solution of 10 ($R_8$=COOH, $R_2$=COCF$_3$; 200 mg, 0.48 mmol) in DCM (4 mL) and DMF (one drop), oxalylchloride (65 mL, 0.72 mmol) was added. The reaction mixture was stirred for 1 hour at room temperature and then concentrated under reduced pressure. The crude acid chloride was dissolved in DCM (1 mL) and added to a solution of amino ethanol (60 mL, 0.96 mmol) and Et$_3$N (130 mL, 0.96 mmol) in DCM (3 mL). The reaction mixture was stirred for 1 hour at room temperature, then quenched with a saturated NaHCO$_3$ solution in H$_2$O and the product was extracted into ethyl acetate. The organics were washed with a saturated NaCl solution in H$_2$O, dried (Na$_2$SO$_4$) and concentrated under reduced pressure. The crude product was purified by column chromatography on silica to give (10: $R_8$=C(O)NHCH$_2$CH$_2$OH, $R_2$=COCF$_3$; 152 mg, 69%).

To a stirred solution of 10 ($R_8$=C(O)NHCH$_2$CH$_2$OH, $R_2$=COCF$_3$; 150 mg, 0.325 mmol) in DCM (5 mL), SOCl$_2$ (90 mL, 0.65 mmol) was added. The reaction mixture was stirred overnight at room temperature. The reaction was quenched with a saturated NaHCO$_3$ solution in H$_2$O and the product was extracted into DCM. The organics were washed with a saturated NaCl solution in H$_2$O, dried over Na$_2$SO$_4$ and concentrated under reduced pressure. The crude product was purified by column chromatography on silica to give rel-2,2,2-trifluoro-N-[(2R,10R,14bR)-8-[4,5-dihydrooxazol-2-yl]-1,2,3,4,10,14b-hexahydro-10-methyldibenzo[c,f]pyrido[1,2-a]azepin-2-yl]acetamide (10: $R_8$=C$_3$H$_4$NO, $R_2$=COCF$_3$; 60 mg, 42%). Data: (m/z)=444 (M+H)$^+$.

Example 52

Rel-2,2,2-trifluoro-N-[(2R,10R,14bR)-1,2,3,4,10,14b-hexahydro-10-methyl-8-nitrodibenzo[c,f]pyrido[1,2-a]azepin-2-yl]acetamide (10: $R_8$=NO$_3$, $R_2$=COCF$_3$)

A solution of 10 ($_8$=H, $R_2$=COCF$_3$; 76 mg, 0.2 mmol) in DCM (1.5 mL) was cooled to 0° C. and fuming nitric acid (21 μl, 0.5 mmol) was added in portions. The ice/water bath was removed and the reaction mixture turned red. After 10 min the reaction was quenched with aqueous NaHCO$_3$, extracted with DCM, dried (Na$_2$SO$_4$) and concentrated under reduced pressure. The crude product was purified by column chromatography on silica (Heptane:Ethyl acetate=7:3) followed by preparative HPLC. Freeze-drying from acetonitrile/H$_2$O afforded rel-2,2,2-trifluoro-N-[(2R,10R,14bR)-1,2,3,4,10,14b-hexahydro-10-methyl-8-nitrodibenzo[c,f]pyrido[1,2-a]azepin-2-yl]acetamide (10, $R_8$=NO$_2$, $R_2$=COCF$_3$; 6 mg, 7%). Data: (m/z)=420 (M+H)$^+$.

Example 53

Rel-2,2,2-trifluoro-N-[(2R,10R,14bR)-8-formyl-1,2,3,4,10,14b-hexahydro-10-methyldibenzo[c,f]pyrido[1,2-a]azepin-2-yl]acetamide (10: $R_8$=CHO, $R_2$=COCF$_3$)

Oxalyl chloride (0.594 mL, 6.8 mmol) was added drop wise to a stirred solution of N,N-dimethylformamide (3.5 mL) at 0° C. The reaction mixture was stirred for 25 min at 0° C. and a white precipitate was formed. A solution of 10 ($R_8$=H, $R_2$=COCF$_3$; 510 mg, 1.36 mmol) in N,N-dimethylformamide (2.5 mL) was then added to the reaction mixture and heated to 70° C. After 1.5 h the reaction mixture was cooled, quenched with aqueous NaHCO$_3$ and the product was extracted into ethyl acetate, dried (Na$_2$SO$_4$) and concentrated under reduced pressure. The crude product was purified by column chromatography on silica (Heptane:Ethyl acetate=7:3) followed by preparative HPLC. Freeze-drying from acetonitrile/H$_2$O afforded rel-2,2,2-trifluoro-N-[(2R,10R,14bR)-8-formyl-1,2,3,4,10,14b-hexahydro-10-methyldibenzo[c,f]pyrido[1,2-a]azepin-2-yl]acetamide (10, $R_8$=CHO, $R_2$=COCF$_3$; 164 mg, 30%). Data: (m/z)=403(M+H)$^+$.

Example 54

Rel-N-[(2R,10R,14bR)-1,2,3,4,10,14b-hexahydro-8-[1-(hydroxyimino)ethyl]-10-methyldibenzo[c,f]pyrido[1,2-a]azepin-2-yl]-4-methyl-1,2,3-thiadiazole-5-carboxamide (10: $R_8$=C(CH$_3$)NOH, $R_2$=COC$_3$H$_3$N$_2$S)

This compound was prepared, in an analogous manner as described in Example 13, from 10 ($R_8$=COCH$_3$, $R_2$=COC$_3$H$_3$N$_2$S) to afford rel-N-[(2R,10R,14bR)-1,2,3,4,10,14b-hexahydro-8-[1-(hydroxyimino)ethyl]-10-methyldibenzo[c,f]pyrido[1,2-a]azepin-2-yl]-4-methyl-1,2,3-thiadiazole-5-carboxamide (10: $R_8$=C(CH$_3$)NOH, $R_2$=COC$_3$H$_3$N$_2$S; 170 mg, 49%). Data: (m/z)=462 (M+H)$^+$.

Example 55

Glucocorticoid Receptor Binding Activity

The affinity of compounds was tested using a Glucocorticoid Receptor Competitor Assay kit (PanVera®). Components of the kit were thawed from −80° C. on ice (Fluormone GS1, recombinant human-GR (GR)) or at room temperature (GR screening buffer, stabilising peptide and DTT). 10 mM test compounds were manually diluted to 20 μM then serially diluted to a final concentration range of 10 μM to 0.1 nM using the BioMek 2000 (Beckman-Coulter) into a black walled 384 welled plate (Matrix technologies). In the following order: fluormone GS1 (1 nM final concentration) is added to all wells excluding the buffer control wells, GR (4 nM final concentration) is added to all wells except minimum and buffer control wells, cortisol (10 μM final concentration) is added to fluormone GS1 control wells only, buffer is added to all wells to a final volume of 40 μl. The plate is covered and incubated at room temperature with agitation for 90 minutes. Readings were taken using the Analyst (LJL) in fluorescence polarisation reading mode. The MilliP ratio is calculated from cps readings obtained in parallel and perpendicular mode. The percent effect of the bound ligand is calculated at each concentration and the dose response curves plotted allowing the $EC_{50}$ to be calculated. This is compared to the known standard (11β,17β)-11-(1,3-benzodioxol-5-yl)-17-hydroxy-17-(1-propynyl)estra-4,9-dien-3-one (CAS No. 189035-07-2), $EC_{50}=10^{-8}$ M). All compounds exemplified have binding activities $<2\times10^{-8}$ M.

Example 56

Functional Responses In Vitro

To quantify the ability of compounds to inhibit inflammatory gene expression in vitro, responses of compounds were evaluated in the human cell line $U_2OS$ that was stably transfected with human recombinant. GR.DNA, $U_2OS$ cells were stimulated with TNFα and IFNγ which leads to the secretion of MCP-1 in the supernatant. Secretion of MCP-1 was quantified indirectly by the use of two anti-human-MCP-1 antibodies, one labeled with the fluorescent donor Europium, the second one labeled with the fluorescent acceptor Allophycocyanin (APC). Secretion of MCP-1 in supernatant is quantified by measuring the emission wavelength of APC (665 nm) when Europium is excitated at 340 nm. The ability of compounds (prednisolone or compounds according to formula I) to inhibit MCP-1 expression was quantified and $EC_{50}$ values were calculated. All compounds exemplified were tested in this assay and have shown potent in vitro anti-inflammatory properties of $<2\times10^{-8}$ M.

Example 57

Anti-Inflammatory Activity In Vivo

The potency of compounds to inhibit inflammation can be quantified in a model in which mice are tested with lipopolysaccharide (LPS). Anti-inflammatory effects can be quantified as inhibition of LPS-induced TNFα (S. R. Hyde & R. E. McCallum, Infection & Immunity, 60; 976-982 (1992)). Mice are treated i.p. with 0.5 mg/kg LPS. Compounds according to formula I are dosed systemically by oral administration at 1 hour before the induction with LPS. 1½ hours after LPS induction, serum is collected and mice are sacrificed. TNFα levels in serum are quantified using a commercially available Elisa-kit according to the descriptions of the supplier. A selection (examples 3, 5, 12, 16, 19, 20, 26, 38, 39, 42, 54) of compounds exemplified were tested in this model. All tested compounds show anti-inflammatory activity in the model with an ED50<10 mg/kg).

Example 58

Anti-Arthritic Activity In Vivo

The ability of compounds to inhibit arthritis can be tested in a Collagen type II-Induced Arthritis model in mice (D. E., Trentham et al. J. Exp Med 146; 857-868 (1977)). In this model male Dba/1 mice are immunized and boosted (after 3 weeks) with Collagen. Arthritis is scored as swelling of paws. Mice that develop arthritis are orally treated for 3 weeks either with prednisolone or compounds according to formula I (the therapeutic model). In the model, further development of arthritis is scored as paw swelling 3 times a week. After 3 weeks, mice are sacrificed. Potency of compounds to inhibit arthritis is quantified as the ability to inhibit paw swelling. A selection (examples 5, 12, 19, 20, 39, 54) of compounds exemplified were tested in this model. All tested compounds show anti-arthritic activity in the model with an ED50<10 mg/kg).

What is claimed is:
1. A compound according to Formula I:

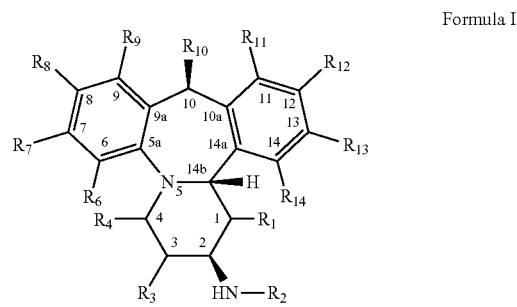

Formula I or a pharmaceutically acceptable salt thereof,
wherein the R groups have the following meanings:
— $R_1$ is —H or —(1-4C)alkyl;
— $R_2$ is —C(O)$R_{15}$ or —SO$_2R_{15}$;
— $R_3$ is —H, —(1-4C) alkyl or —OR$_{16}$;
— $R_4$ is —H, —(1-4C)alkyl or —OR$_{16}$;
— $R_6$ is —H or —C($R_{16}$)NOR$_{16}$;
— $R_7$ is —H, -halogen, -cyano;
—(1-6C) alkyl, —(2-6C)alkenyl or —(2-6C)alkynyl, all optionally substituted with amino, -hydroxyl or -halogen;
— $R_8$ is —H, -cyano, -halogen, -nitro;
—(1-6C) alkyl, —(2-6C)alkenyl, —(2-6C)alkynyl or —O(1-6C)alkyl, all optionally substituted with -amino, -hydroxyl or -halogen;
-(hetero)aryl, optionally substituted with -cyano, -halogen, —(1-4C)alkyl, —(1-4C)alkoxy, —(1-4C)alkoxy(1-4C)alkyl or -(hetero)aryl;
—C($R_{16}$)NOR$_{16}$, —C(O)N($R_{17}$)$_2$, —C(O)$R_{18}$, —C(O)OR$_{19}$, —NHC(O)$R_{20}$, or —NHS(O)$_2R_{21}$;
— $R_9$ is —H, -halogen, -cyano, or —(1-4C)alkyl, optionally substituted with -halogen;
— $R_{10}$ is —(1-4C)alkyl;
— $R_{11}$ is —H;
— $R_{12}$ is —H, -cyano or —(1-4C)alkyl;
— $R_{13}$ is —H, —(1-4C)alkyl, -halogen or -formyl;
$R_{14}$ is —H, -halogen, -cyano, —(1-4C)alkyl or -(hetero)aryl;
— $R_{15}$ is —H;

—(1-6C)alkyl, —(2-6C)alkenyl, —(2-6C)alkynyl, —O(2-6C)alkyl, -O(2-6C)alkenyl or —O(2-6C)alkynyl, all optionally substituted with one or more —OH, -halogen, -cyano or -(hetero)aryl;

-(hetero)aryl, optionally substituted with —(1-4C)alkyl, -halogen or —NH$_2$;

—NH$_2$, —(di)(1-4C)alkylamino, —(1-4C)alkylthio(1-4C)alkyl, —(1-4C)alkoxy(1-4C)alkyl or —NR$_{16}$OR$_{16}$;

—R$_{16}$ is —H, —(1-6C)alkyl, —(2-6C)alkenyl or —(2-6C)alkynyl;

—R$_{17}$ is —H;

—(1-6C)alkyl, optionally substituted with -halogen, —(1-4C)alkoxy or -(hetero)aryl, optionally substituted with -halogen, —(1-4C)alkyl or —(1-4C)alkoxy;

—(3-6C)cycloalkyl or -(hetero)aryl, optionally substituted with -halogen, —(1-4C)alkyl or —(1-4C)alkoxy;

—R$_{18}$ is —H, —NH$_2$ or —(1-4C)alkyl, optionally substituted with —OH, -halogen, -cyano or —S(1-4C)alkyl;

—R$_{19}$ is —H or —(1-6C)alkyl, optionally substituted with —OH or -halogen; and —R$_{20}$ is —H;

—(1-6C)alkyl or —(2-6C)alkenyl, both optionally substituted by -halogen, —O(1-6C)alkyl, -(hetero)aryl, optionally substituted with —(1-4C)alkyl or halogen;

—(3-6C)cycloalkyl, —(1-6C)alkoxy; or

-(hetero)aryl, optionally substituted with —(1-4C)alkyl); —NH$_2$, —NH(1-6C)alkyl or —NH(hetero)aryl);

—R$_{21}$ is —H or —(1-6C)alkyl.

2. A compound according to claim 1 wherein —R$_3$, —R$_6$, —R$_7$, —R$_9$, —R$_{12}$, —R$_{13}$, —R$_{14}$ and —R$_{16}$ are —H and —R$_4$ are —H or —(1-4C)alkyl.

3. A compound according to claim 1, wherein
—R$_1$ is —H;
—R$_8$ is —H, -cyano or -halogen;
-(hetero)aryl, optionally substituted with —(1-4C)alkyl;
—C(R$_{16}$)NOR$_{16}$, —C(O)N(R$_{17}$)$_2$, —C(O)R$_{18}$ or —C(O)OR$_{19}$;
—R$_{10}$ is —(1-4C)alkyl;
—R$_{15}$ is —(1-6C)alkyl, optionally substituted with one or more -halogen or -(hetero)aryl;
-(hetero)aryl, optionally substituted with —(1-4C)alkyl or —NH$_2$; or —(di)(1-4C)alkylamino;
—R$_{17}$ is -(hetero)aryl, optionally substituted with —(1-4C)alkoxy;
—R$_{18}$ is —(1-4C)alkyl and
—R$_{19}$ is —(1-6C)alkyl.

4. A compound selected from the group of
rel-N-[(2R,10R,14bR)-8-bromo-1,2,3,4,10,14b-hexahydro-10-methyldibenzo[c,f]pyrido[1,2-a]azepin-2-yl]-2,2,2-trifluoroacetamide;
rel-N-[(2R,10R,14bR)-8-cyano-1,2,3,4,10,14b-hexahydro-10-methyldibenzo[c,f]pyrido[1,2-a]azepin-2-yl]-2,2,2-trifluoroacetamide;
rel-2,2-dichloro-N-[(2R,10R,14bR)-8-cyano-1,2,3,4,10,14b-hexahydro-10-methyldibenzo[c,f]pyrido[1,2-a]azepin-2-yl]acetamide;
rel-2,2,2-trifluoro-N-[(2R,10R,14bR)-1,2,3,4,10,14b-hexahydro-10-methyldibenzo[c,f]pyrido[1,2-a]azepin-2-yl]acetamide
rel-N-[(2R,10R,14bR)-8-cyano-1,2,3,4,10,14b-hexahydro-10-methyldibenzo[c,f]pyrido[1,2-a]azepin-2-yl]-4-methyl-1,2,3-thiadiazole-5-carboxamide;
rel-N-[(2R,10R,14bR)-8-cyano-1,2,3,4,10,14b-hexahydro-10-methyldibenzo[c,f]pyrido[1,2-a]azepin-2-yl]-2,2-difluoroacetamide;
rel-N-[(2R,10R,14bR)-8-cyano-1,2,3,4,10,14b-hexahydro-10-methyldibenzo[c,f]pyrido[1,2-a]azepin-2-yl]methanesulfonamide;
rel-N-[(2R,10R,14bR)-8-cyano-1,2,3,4,10,14b-hexahydro-10-methyldibenzo[c,f pyrido[1,2-a]azepin-2-yl]ethanesulfonamide;
rel-N'-[(2R,10R,14bR)-8-cyano-1,2,3,4,10,14b-hexahydro-10-methyldibenzo[c,f]pyrido[1,2-a]azepin-2-yl]-N,N-dimethylaminosulfamide;
rel-N-[(2R,10R,14bR)-8-cyano-1,2,3,4,10,14b-hexahydro-10-methyldibenzo[c,f]pyrido[1,2-a]azepin-2-yl]-3,5-dimethylisoxazole-4-carboxamide;
rel-N-[(2R,10R,14bR)-8-acetyl-1,2,3,4,10,14b-hexahydro-10-methyldibenzo[c,f]pyrido[1,2-a]azepin-2-yl]-2,2,2-trifluoroacetamide;
rel-N-[(2R,10R,14bR)-8-acetyl-1,2,3,4,10,14b-hexahydro-10-methyldibenzo[c,f]pyrido[1,2-a]azepin-2-yl]-4-methyl-1,2,3-thiadiazole-5-carboxamide;
rel-2,2,2-trifluoro-N-[(2R,10R,14bR)-1,2,3,4,10,14b-hexahydro-8-[1-(hydroxyimino)ethyl]-10-methyldibenzo[c,f]pyrido[1,2-a]azepin-2-yl]acetamide;
rel-2,2,2-trifluoro-N-[(2R,10R,14bR)-1,2,3,4,10,14b-hexahydro-10-methyl-8-(pyridin-4-yl)dibenzo[c,f]pyrido[1,2-a]azepin-2-yl]acetamide;
rel-2,2-dichloro-N-[(2R,10R,14bR)-1,2,3,4,10,14b-hexahydro-10-methyl-8-(pyridin-4-yl)dibenzo[c,f]pyrido[1,2-a]azepin-2-yl]acetamide;
rel-2-chloro-2,2-difluoro-N-[(2R,10R,14bR)-1,2,3,4,10,14b-hexahydro-10-methyl-8-(pyridin-4-yl)dibenzo[c,f]pyrido[1,2-a]azepin-2-yl]acetamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]acetamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]isoxazole-5-carboxamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]-5-methyl-isoxazole-3-carboxamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]-4-methyl-1,2,3-thiadiazole-5-carboxamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]-2-thiophenacetamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]methanesulfonamide;
rel-N-[(2R,10R,14bR)-1,2,3,4,10,14b-hexahydro-10-methyl-8-(pyridin-4-yl)dibenzo[c,f]pyrido[1,2-a]azepin-2-yl]ethanesulfonamide;
rel-N'-[(2R,10R,14bR)-1,2,3,4,10,14b-hexahydro-10-methyl-8-(pyridin-4-yl)dibenzo[c,f]pyrido[1,2-a]azepin-2-yl]-N,N-dimethylaminosulfamide;
rel-2,2-difluoro-N-[(2R,10R,14bR)-1,2,3,4,10,14b-hexahydro-10-methyl-8-(pyridin-4-yl)dibenzo[c,f]pyrido[1,2-a]azepin-2-yl]acetamide;
rel-4-amino-N-[(2R,10R,14bR)-1,2,3,4,10,14b-hexahydro-10-methyl-8-(pyridin-4-yl)dibenzo[c,f]pyrido[1,2-a]azepin-2-yl]-1,2,5-oxadiazole-3-carboxamide;
rel-2,2,2-trifluoro-N-[(2R,10R,14bR)-1,2,3,4,10,14b-hexahydro-10-methyl-8-(pyrimidin-2-yl)dibenzo[c,f]pyrido[1,2-a]azepin-2-yl]acetamide;
rel-N-[(2R,10R,14bR)-1,2,3,4,10,14b-hexahydro-10-methyl-8-(pyrimidin-2-yl)dibenzo[c,f]pyrido[1,2-a]azepin-2-yl]-4-methyl-1,2,3-thiadiazole-5-carboxamide;

rel-2,2,2-trifluoro-N-[(2R,10R,14bR)-1,2,3,4,10,14b-hexahydro-10-methyl-8-(pyrazin-2-yl)dibenzo[c,f]pyrido[1,2-a]azepin-2-yl]acetamide;

methyl rel-(2R,10R,14bR)-1,2,3,4,10,14b-hexahydro-10-methyl-2-(2,2,2-trifluoroacetylamino)dibenzo[c,f]pyrido[1,2-a]azepine-8-carboxylate;

ethyl rel-(2R,10R,14bR)-1,2,3,4,10,14b-hexahydro-10-methyl 2-(2,2,2-trifluoroacetylamino)dibenzo[c,f]pyrido[1,2-a]azepine-8-carboxylate;

propyl rel-(2R,10R,14bR)-1,2,3,4,10,14b-hexahydro-10-methyl 2-(2,2,2-trifluoroacetylamino)dibenzo[c,f]pyrido[1,2-a]azepine-8-carboxylate;

rel-(2R,10R,14bR)-1,2,3,4,10,14b-hexahydro-10-methyl-N-phenyl-2-(2,2,2-trifluoroacetylamino)dibenzo[c,f]pyrido[1,2-a]azepine-8-carboxamide;

rel-(2R,10R,14bR)-1,2,3,4,10,14b-hexahydro-10-methyl-N-(pyridin-4-yl)-2-(2,2,2-trifluoroacetylamino)dibenzo[c,f]pyrido[1,2-a]azepine-8-carboxamide;

rel-(2R,10R,14bR)-1,2,3,4,10,14b-hexahydro-N-(2-methoxypyrimidin-5-yl)-10-methyl-2-(2,2,2-trifluoroacetylamino)dibenzo[c,f]pyrido[1,2-a]azepine-8-carboxamide;

rel-(2R,10R,14bR)-1,2,3,4,10,14b-hexahydro-N-(2-methoxyphenyl)-10-methyl-2-(2,2,2-trifluoroacetylamino)-dibenzo[c,f]pyrido[1,2-a]azepine-8-carboxamide;

rel-2,2,2-trifluoro-N-[(2R,10R,14bR)-1,2,3,4,10,14b-hexahydro-10-methyl-8-(2-ethyltetrazol-5-yl)dibenzo[c,f]pyrido[1,2-a]azepin-2-yl]acetamide;

rel-2-chloro-2,2-difluoro-N-[(2R,10R,14bR)-1,2,3,4,10,14b-hexahydro-10-methyl-8-(2-methyltetrazol-5-yl)dibenzo[c,f]pyrido[1,2-a]azepin-2-yl]acetamide;

rel-N-[(2R,10R,14bR)-1,2,3,4,10,14b-hexahydro-10-methyl-8-(2-methyltetrazol-5-yl)dibenzo[c,f]pyrido[1,2-a]azepin-2-yl]-4-methyl-1,2,3-thiadiazole-5-carboxamide;

rel-2,2,2-trifluoro-N-[(2R,10R,14bR)-1,2,3,4,10,14b-hexahydro-10-methyl-8-(pyrimidin-4-yl)dibenzo[c,f]pyrido[1,2-a]azepin-2-yl]acetamide;

rel-2,2,2-trifluoro-N-[(2R,10R,14bR)-1,2,3,4,10,14b-hexahydro-10-methyl-8-(pyridin-2-yl)dibenzo[c,f]pyrido[1,2-a]azepin-2-yl]acetamide;

rel-N-[(2R,10R,14bR)-1,2,3,4,10,14b-hexahydro-10-methyl-8-(pyrimidin-4-yl)dibenzo[c,f]pyrido[1,2-a]azepin-2-yl]-4-methyl-1,2,3-thiadiazole-5-carboxamide;

rel-2,2-chloro-N-[(2R,10R,14bR)-1,2,3,4,10,14b-hexahydro-10-methyl-8-(pyrimidin-4-yl)dibenzo[c,f]pyrido[1,2-a]azepin-2-yl]acetamide;

rel-N-[(2R,10R,14bR)-1,2,3,4,10,14b-hexahydro-10-methyl-8-(pyrimidin-4-yl)dibenzo[c,f]pyrido[1,2-a]azepin-2-yl]methanesulfonamide;

rel-2-chloro-2,2-difluoro-N-[(2R,10R,14bR)-1,2,3,4,10,14b-hexahydro-10-methyl-8-(pyrimidin-4-yl)dibenzo[c,f]pyrido[1,2-a]azepin-2-yl]acetamide;

rel-5-amino-N-[(2R,10R,14bR)-1,2,3,4,10,14b-hexahydro-10-methyl-8-(pyrimidin-4-yl)dibenzo[c,f]pyrido[1,2-a]azepin-2-yl]-1,2,5-oxadiazole-4-carboxamide;

rel-2,2,2-trifluoro-N-[(2R,4S,10R,14bR)-1,2,3,4,10,14b-hexahydro-4,10-dimethyldibenzo[c,f]pyrido[1,2-a]azepin-2-yl]acetamide;

rel-N-[(2R,10R,14bR)-8-cyano-1,2,3,4,10,14b-hexahydro-10-methyldibenzo[c,f]pyrido[1,2-a]azepin-2-yl]-N'-methyl-N'-methoxyurea;

rel-N-[(2R,10R,14bR)-8-cyano-1,2,3,4,10,14b-hexahydro-10-methyldibenzo[c,f]pyrido[1,2-a]azepin-2-yl]-2-hydroxyacetamide;

rel-(2R,10R,14bR)-2-[(N,N-dimethylaminocarbonyl)amino]-1,2,3,4,10,14b-hexahydro-10-methyl-N-phenyldibenzo[c,f]pyrido[1,2-a]azepine-8-carboxamide;

rel-2,2,2-trifluoro-N-[(2R,10R,14bR)-8-[4,5-dihydrooxazol-2-yl]-1,2,3,4,10,14b-hexahydro-10-methyldibenzo[c,f]pyrido[1,2-a]azepin-2-yl]acetamide;

rel-2,2,2-trifluoro-N-[(2R,10R,14bR)-1,2,3,4,10,14b-hexahydro-10-methyl-8-nitrodibenzo[c,f]pyrido[1,2-a]azepin-2-yl]acetamide;

rel-2,2,2-trifluoro-N-[(2R,10R,14bR)-8-formyl-1,2,3,4,10,14b-hexahydro-10-methyldibenzo[c,f]pyrido[1,2-a]azepin-2-yl]acetamide; or rel-N-[(2R,10R,14bR)-1,2,3,4,10,14b-hexahydro-8-[1-(hydroxyimino)ethyl]-10-methyldibenzo[c,f]pyrido[1,2-a]azepin-2-yl]-4-methyl-1,2,3-thiadiazole-5-carboxamide.

5. A pharmaceutical composition which comprises a compound of formula I according to claim 1 or a pharmaceutically acceptable salt thereof and one or more pharmaceutically acceptable excipients.

6. A method for treating a disease, condition or disorder responsive to glucocorticoid receptor activity, wherein the disease, condition or disorder is selected from the group consisting of rheumatic disease, dermatological disease, allergic disorder, pulmonary condition and immune and inflammatory disease, the method comprising administering to an individual a therapeutically effective amount of a compound of formula I according to claim 1 or a pharmaceutically acceptable salt thereof.

7. The method of claim 6, wherein the disease is rheumatoid disease.

8. The method of claim 7, wherein the rheumatoid disease is selected from the group consisting of rheumatoid arthritis, juvenile arthritis and ankylosing spoldylitis.

9. The method of claim 6, wherein the condition is a pulmonary condition selected from the group consisting of asthma and chronic obstructive pulmonary disease.

10. The method of claim 6, wherein the dermatological disease is selected from the group consisting of psoriasis and pemphigus.

11. The method of claim 6, wherein the allergic disorder is selected from the group consisting of allergic rhinitis, atopic dermatitis and contact dermatitis.

12. The method of claim 6, wherein the immune and inflammatory disease is selected from the group consisting of Crohn disease, ulcerative colitis, systemic lupus erythematosus, autoimmune chronic active hepatitis, osteoarthritis, tendonitis and bursitis.

* * * * *

UNITED STATES PATENT AND TRADEMARK OFFICE
CERTIFICATE OF CORRECTION

| | | |
|---|---|---|
| PATENT NO. | : 8,575,152 B2 | Page 1 of 1 |
| APPLICATION NO. | : 12/065241 | |
| DATED | : November 5, 2013 | |
| INVENTOR(S) | : Plate et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1409 days.

Signed and Sealed this
Twenty-fourth Day of February, 2015

Michelle K. Lee
*Deputy Director of the United States Patent and Trademark Office*